US008530457B2

(12) United States Patent  
Henske et al.

(10) Patent No.: US 8,530,457 B2  
(45) Date of Patent: Sep. 10, 2013

(54) METHOD FOR THE TREATMENT OF LYMPHANGIOLEIOMYOMATOSIS (LAM)

(75) Inventors: Elizabeth Petri Henske, Cambridge, MA (US); Jane Yu, Brighton, MA (US)

(73) Assignee: Fox Chase Cancer Center, Philadelphia, PA (US)

( * ) Notice: Subject to any disclaimer, the term of this patent is extended or adjusted under 35 U.S.C. 154(b) by 218 days.

(21) Appl. No.: 12/989,529

(22) PCT Filed: May 20, 2009

(86) PCT No.: PCT/US2009/044643  
§ 371 (c)(1),  
(2), (4) Date: Oct. 25, 2010

(87) PCT Pub. No.: WO2009/143224  
PCT Pub. Date: Nov. 26, 2009

(65) Prior Publication Data  
US 2011/0038800 A1 Feb. 17, 2011

Related U.S. Application Data

(60) Provisional application No. 61/054,714, filed on May 20, 2008.

(51) Int. Cl.  
*A01N 37/28* (2006.01)  
*A01N 37/18* (2006.01)  
*A61K 31/33* (2006.01)  
*A61K 31/19* (2006.01)  
*A61K 31/16* (2006.01)  
*A61K 31/165* (2006.01)

(52) U.S. Cl.  
USPC ............ 514/183; 514/575; 514/613; 514/617

(58) Field of Classification Search  
USPC .......................................... 514/575, 613, 617  
See application file for complete search history.

(56) References Cited

U.S. PATENT DOCUMENTS

| | | | |
|---|---|---|---|
| 6,821,963 B2 | 11/2004 | Barrett et al. | |
| 7,169,816 B2 * | 1/2007 | Barrett et al. | 514/615 |
| 2005/0222163 A1 | 10/2005 | Eck et al. | |
| 2007/0197617 A1 | 8/2007 | Chen et al. | |

FOREIGN PATENT DOCUMENTS

WO 9901426 1/1999

OTHER PUBLICATIONS

Hohman D.W., et al. Lymphangioleiomyomatosis: A review. European Journal of Internal Medicine. vol. 18, pp. 319-324. Published online Dec. 26, 2007.*  
Bissler, J.J., et al. NEJM vol. 358, pp. 140-151. Published Jan. 2008.*  
Thomas Carsillo et al., "Mutations in the tuberous sclerosis complex gene TSC2 are a cause of sporadic pulmonary lymphangioleiomyomatosis", PNAS, 97(11) 6085-6090 (2000).

Lisa C. Costello et al., "High Frequency of Pulmonary Lymphangioleiomyomatosis in Women With Tuberous Sclerosis Complex", Mayo Clin. Proc., 75: 591-594 (2000).  
Peter B. Crino et al., "The Tuberous Sclerosis Complex", N. Engl. J. Med., 355: 1345-56 (2006).  
Denise M. Crooks et al., "Molecular and genetic analysis of disseminated neoplastic cells in lymphangioleiomyomatosis", PNAS, 101(50): 17462-17467 (2004).  
Lynn B. Eckert et al., "Involvement of Ras Activation in Human Breast Cancer Cell Signaling, Invasion, and Anoikis", Cancer Research, 64: 4585-4592 (2004).  
David Neal Franz et al., "Mutational and Radiographic Analysis of Pulmonary Disease Consistent with Lymphangioleiomyomatosis and Micronodular Pneumocyte Hyperplasia in Women with Tuberous Sclerosis", Am. J. Respir. Crit. Care Med., 164: 661-668 (2001).  
Nisreen El-Hashemite et al., "Estrogen Enhanced whereas Tamoxifen Retards Development of Tsc Mouse Liver Hemangioma: A Tumor Related to Renal Angiomyolipoma and Pulmonary Lymphangioleiomyomatosis", Cancer Res., 65(6): 2474-2481 (2005).  
Nisreen El-Hashemite et al., "Mutation in TSC2 and activation of mammalian target of rapamycin signalling pathway in renal angiomyolipoma", The Lancet, 361: 1348-1349 (2003).  
Geraldine A. Finlay et al., "Estrogen-induced Smooth Muscle Cell Growth is Regulated by Tuberin and Associated with Altered Activation of Platelet-derived Growth Factor Receptor-B and ERK-1/2", The Journal of Biological Chemistry, The Journal of Biological Chemistry, 279(22): 23114-23122 (2004).  
G. A. Finlay et al., "Regulation of PDGF production and ERK activation by estrogen is associated with TSC2 gene expression", Am. J. Physiol. Cell Physiol., 285: C409-C418 (2003).  
Douglas Hanahan et al., "The Hallmarks of Cancer", Cell, 100: 57-70 (2000).  
Susan R. Howe et al., "Rodent Model of Reproductive Tract Leiomyomata", Am. J. Pathol., 146(6): 1568-1579 (1995).  
Susan R. Howe et al., "Estrogen Stimulation and Tamoxifen Inhibition of Leiomyoma Cell Growth In Vitro and In Vivo", Endocrinology, Endocrinology, 136(11): 4996-5003 (1995).  
Edward Im et al., "Rheb is in a high activation state and inhibits B-Raf kinase in mammalian cells", Oncogene, 21: 6356-6365 (2002).  
Magdalena Karbowniczek et al., "Recurrent Lymphangiomyomatosis after Transplantation", Am. J. Respir. Crit. Care Med., 167: 976-982 (2003).  
Magdalena Karbowniczek et al., "Regulation of B-Raf Kinase Activity by Tuberni and Rheb is Mammalian Target of Rapamycin (mTOR)-independent", J. Biol. Chem., 279(29): 29930-29937 (2004).

(Continued)

Primary Examiner — Paul Zarek  
Assistant Examiner — George W Kosturko  
(74) Attorney, Agent, or Firm — Patrick J. Hagan; Dann, Dorfman, Herrell and Skillman, P.C.

(57) ABSTRACT

Treatment of lymphangioleiomyomatosis with the MEK1/2 inhibitor CI-1040 delayed the development of primary tumors and blocked the estrogen-induced lung metastases in treated animals. Such treatment also reduced the number of circulating ELT3 cells and decreased their lung colonization after intravenous injection.

8 Claims, 19 Drawing Sheets

(56) References Cited

OTHER PUBLICATIONS

Magdalena Karbowniczek et al., "Renal Angiomyolipomas from Patients with Sporadic Lymphangiomyomatosis Contain Both Neoplastic and Non-Neoplastic Vascular Structures", American Journal of Pathology, 162 (2): 491-500 (2003).
Magdalena Karbowniczek et al., "Rheb Inhibits C-Raf Activity and B-Raf/C-Raf Heterodimerization", J. Biol. Chem., 281(35): 25447-25456 (2006).
Kenneth J. Livak et al., "Analysis of Relative Gene Expression Data Using Real-Time Quantitative PCR and the 2 Method", Methods, 25: 402-408 (2001).
Helen Logginidou et al., "Frequent Estrogen and Progesterone Receptor Immunoreactivity in Renal Angiomyolipomas from Women with Pulmonary Lymphangioleiomyomatosis", Chest, 117: 25-30 (2000).
A. Migliaccio et al., "Tyrosine kinase/p21ras/MAP-kinase pathway activation by estradiol-receptor complex in MCF-7 cells", The EMBO Journal, 15(6): 1292-1300 (1996).
Tracey L. Plank et al., "Hamartin, the Product of the Tuberous Sclerosis 1 (TSC1) Gene, Interacts with Tuberin and Appears to be Localized to Cytoplasmic Vesicles", Can. Res., 58: 4766-4770 (1998).
M. A. Christine Pratt et al., "Estrogen activated raf-1 kinase and induces expression of Egr-1 in MCF-7 breast cancer cells", Molecular and Cellular Biochemistry, 189: 119-125 (1998).
Mahnaz Razandi et al., "Proximal Events in Signaling by Plasma membrane Estrogen Receptors", J. Biol. Chem., 278(4): 2701-2712 (2003).
Mauricio J. Reginato et al., "Integrins and EGFR coordinately regulate the pro-apoptotic protein Bim to prevent anoikis", Nature Cell Biology, 5(8): 733-741 (2003).
Marjatta Rytomaa et al., "Involvement of FADD and caspase-8 signalling in detachment-induced apoptosis", Curr. Biol., 9: 1043-1046 (1999).
Almut Schulze et al., "Analysis of the transcriptional program induced by Raf in epithelial cells", Genes & Development, 15: 981-994 (2001).
Judith S. Sebolt-Leopold et al., "Blockade of the MAP kinase pathway suppresses growth of colon tumors in vivo", Nature Medicine, 5(7): 810-816 (1999).
Charles W. Shepherd et al., "Causes of Death in Patients With Tuberous Sclerosis", Mayo Clin. Proc., 66: 792-796 (1991).
Marjon Van Slegtenhorst et al., "Interaction between hamartin and tuberin, the TSC1 and TSC2 gene products", Human Molecular Genetics, 7(6): 1053-1057 (1998).
Robert X.-D. Song et al., "Estrogen Signaling via a Linear Pathway Involving Insulin-Like Growth Factor I Receptor, Matrix Metalloproteinases, and Epidermal Growth Factor Receptor to Activate Mitogen-Activated Protein Kinase in MCF-7 Breast Cancer Cells", Endocrinology, 148(8): 4091-4101 (2007).
Robert X.-D. Song et al., "Linkage of Rapid Estrogen Action to MAPK Activation by ER alpha-Shc Association and Shc Pathway Activation", Molecular Endocrinology, 16(1): 116-127 (2002).
Eugene J. Sullivan, "Lymphangioleiomyomatosis—A Review", Chest, 114: 1689-1703 (1998).
Ting-Ting Tan et al., "Key roles of BIM-driven apoptosis in epithelial tumors and rational chemotherapy", Cancer Cell, 7: 227-238 (2005).
Jane Yu et al., "Chromosome 16 Loss of Heterozygosity in Tuberous Sclerosis and Sporadic Lymphangiomyomatosis", Am. J. Respir. Crit. Care Med., 164: 1537-1540 (2001).
Jane Yu et al., "Estradiol and tamoxifen stimulate LAM-associated angiomyolipoma cell growth and activate both genomic and nongenomic signaling pathways", Am. J. Physiol. Lung Cell Mol. Physiol., 286: L694-L700 (2004).
Jane J. Yu et al., "Estrogen promotes the survival and pulmonary metastasis of tuberin-null cells", PNAS, 106(8): 2635-2640 (2009).

* cited by examiner

Fig 1 – cont'd
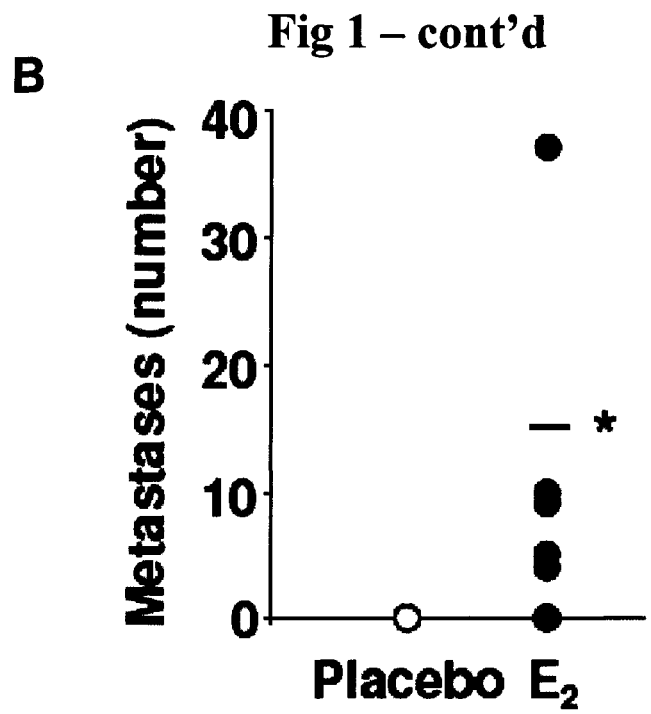
*Ovariectomized Female Mice*
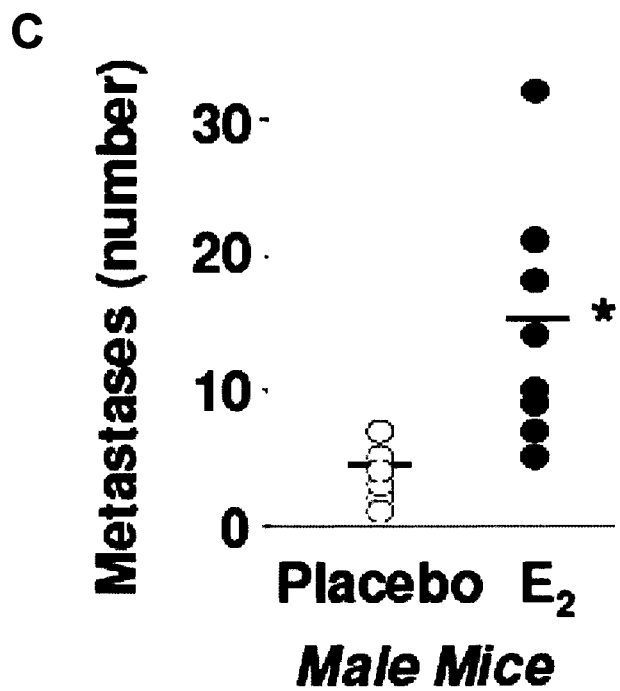
*Male Mice*

Fig. 2 – cont'd
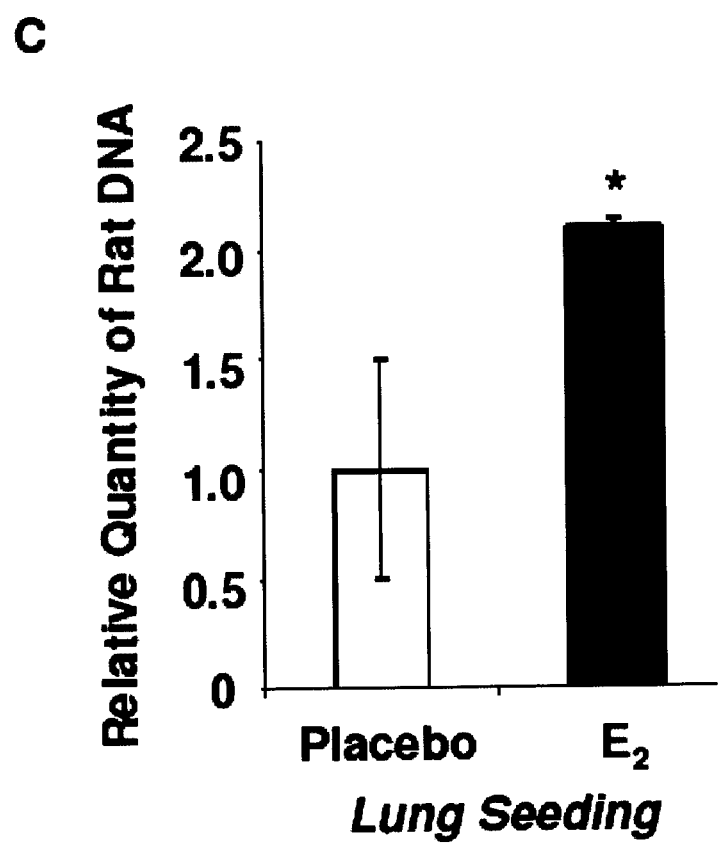

Fig. 3 – cont'd
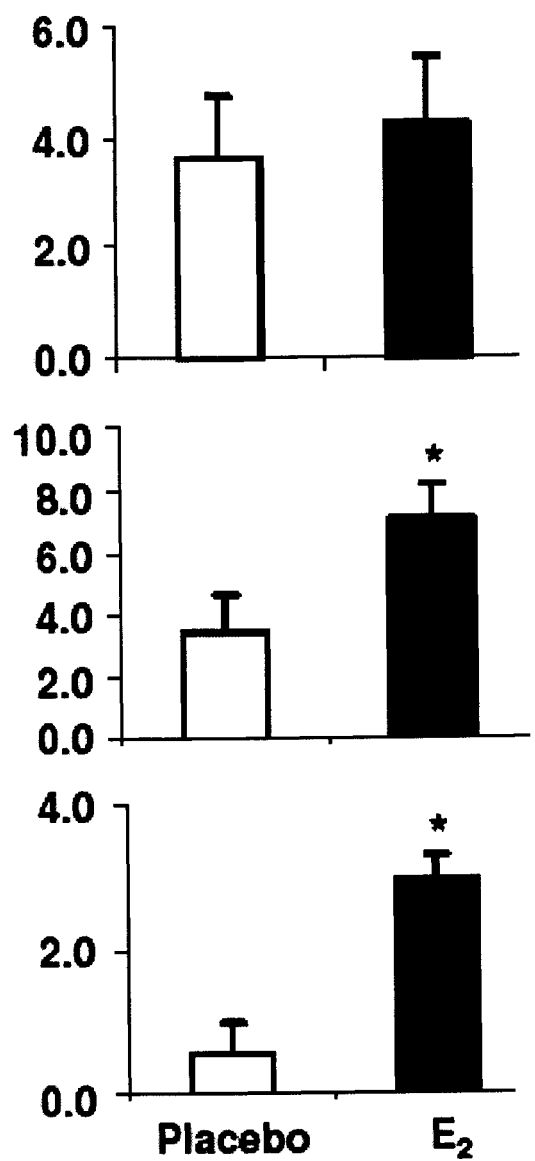

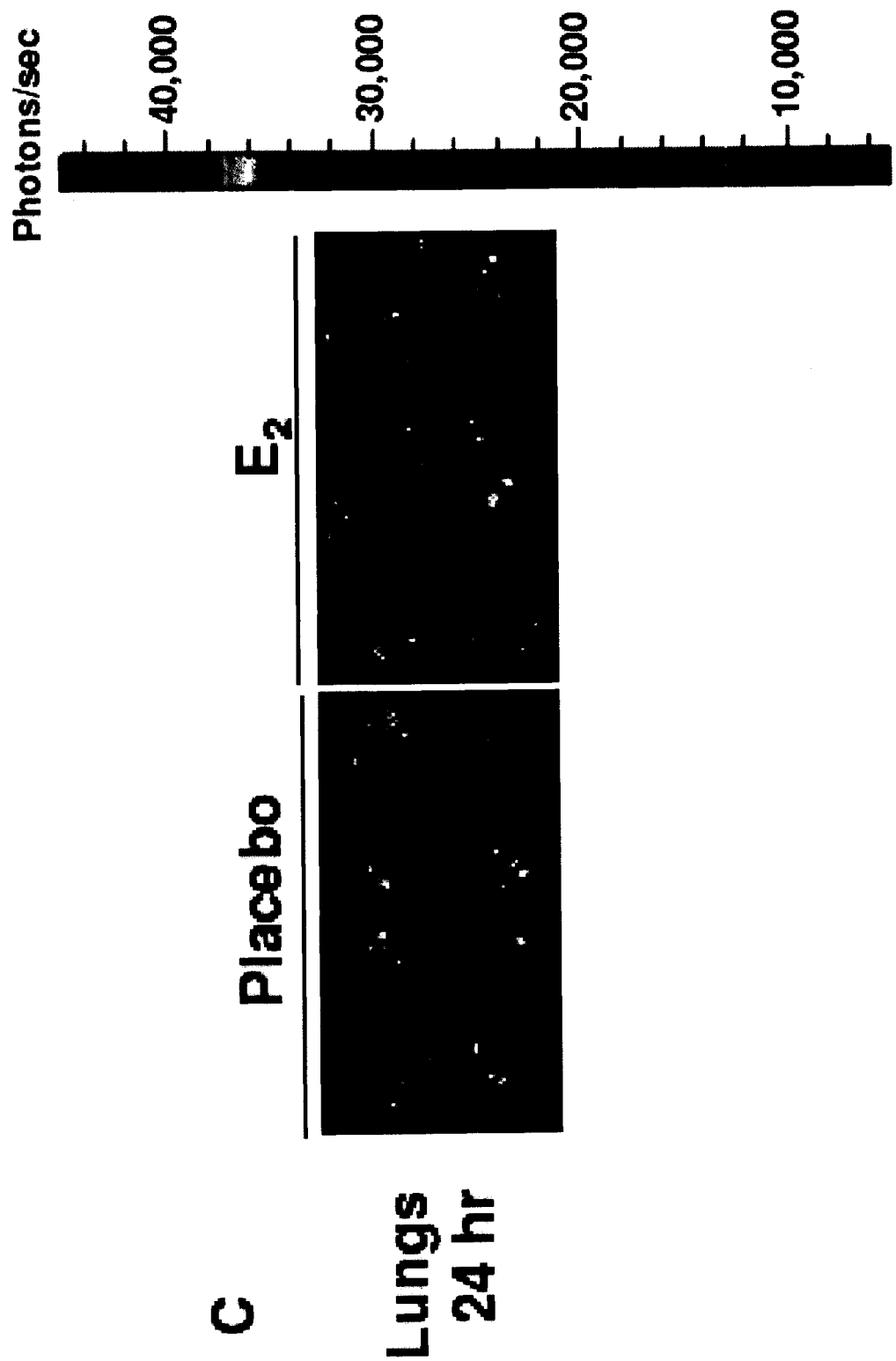
Fig. 3 – cont'd

A

B

Fig. 4 – cont'd
C
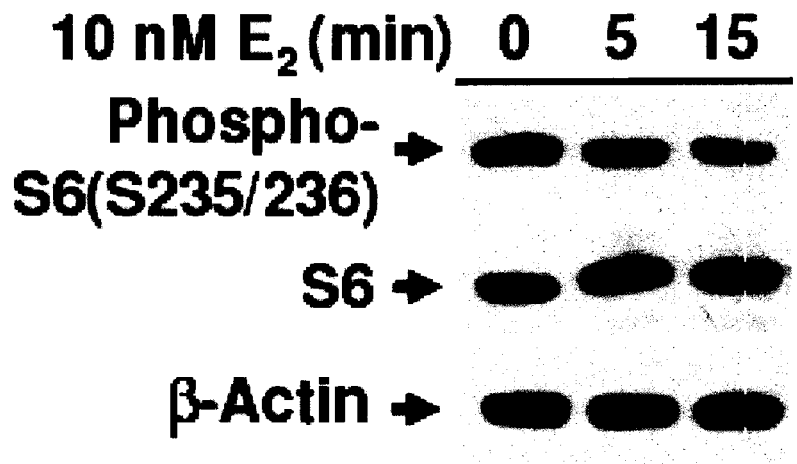
D
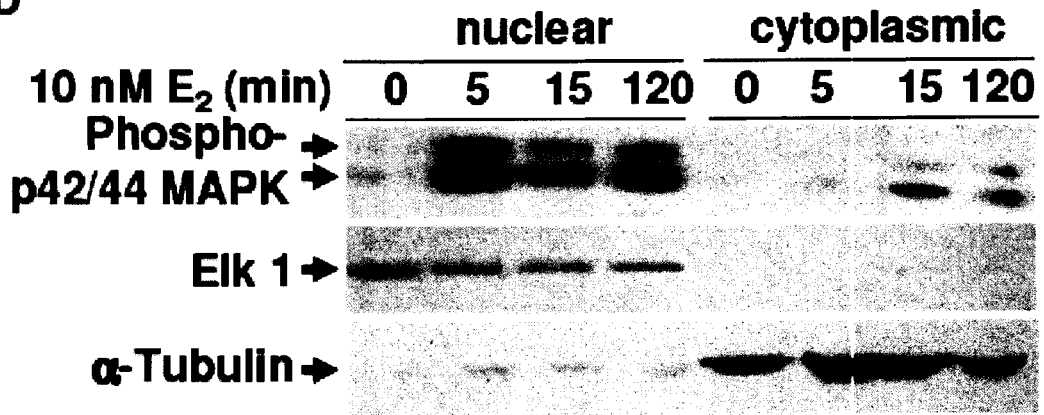

Fig. 4 – cont'd
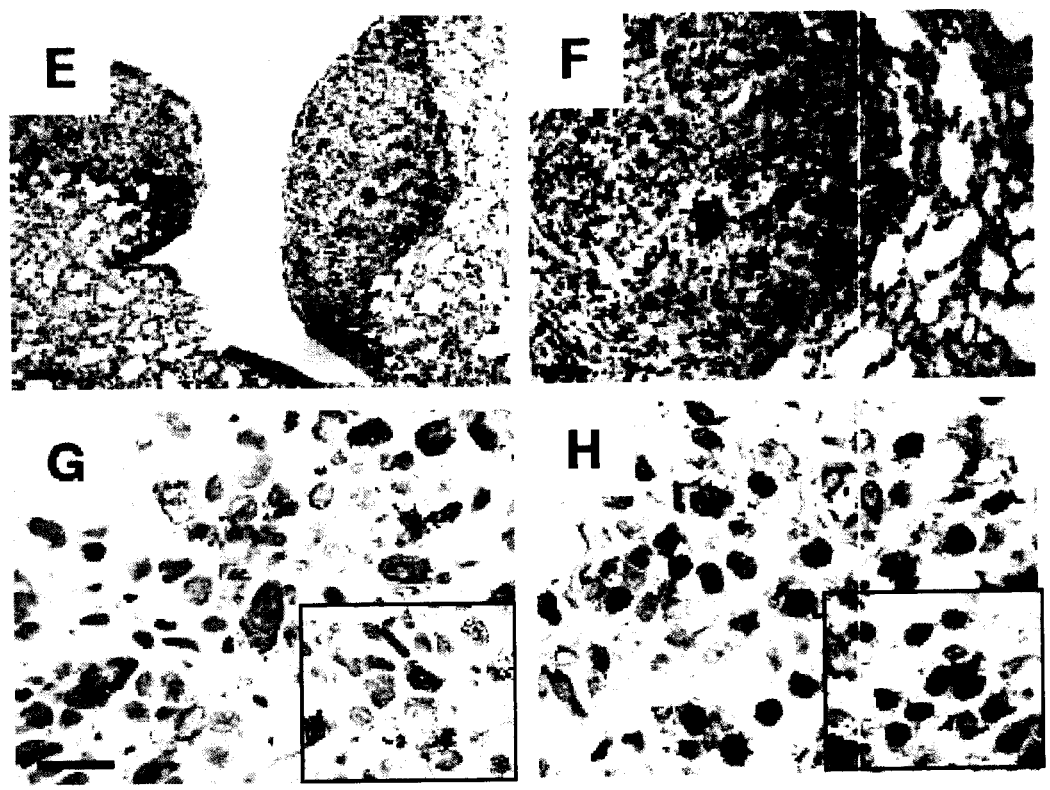
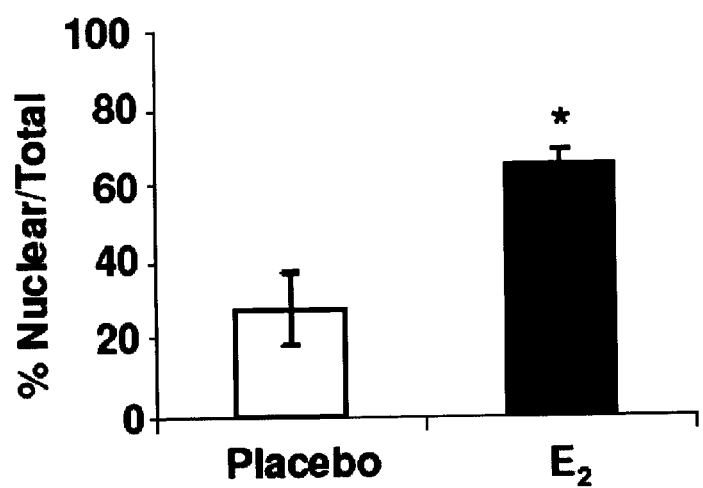

A

B

Fig. 5 – cont'd
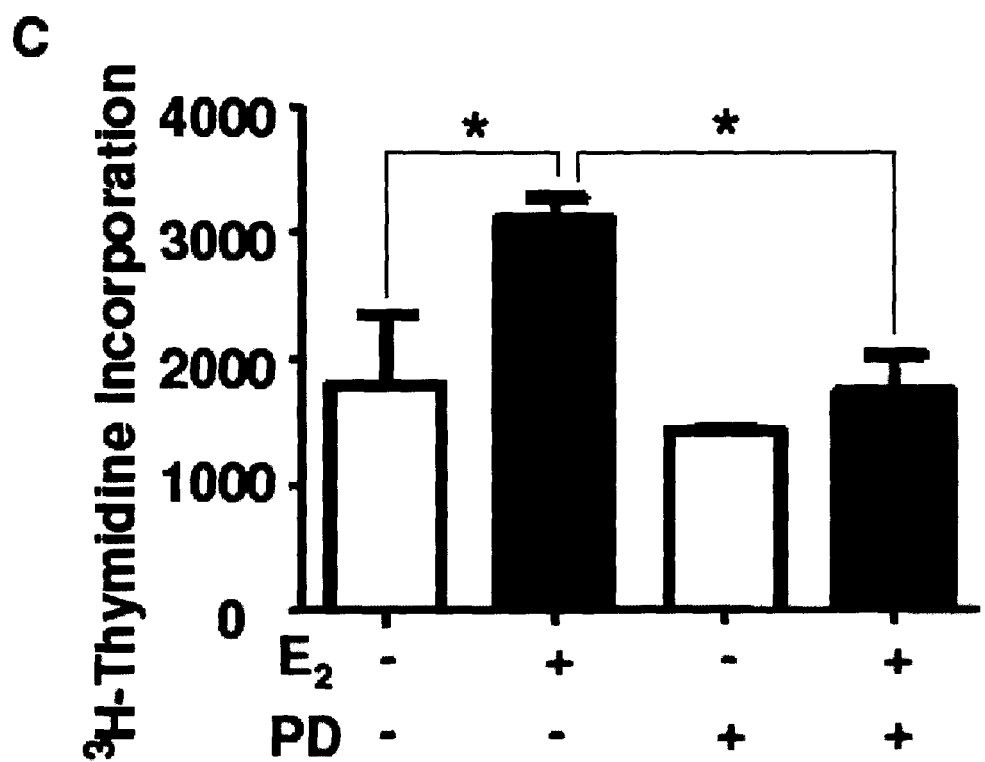

A

B

Fig. 6 –cont'd
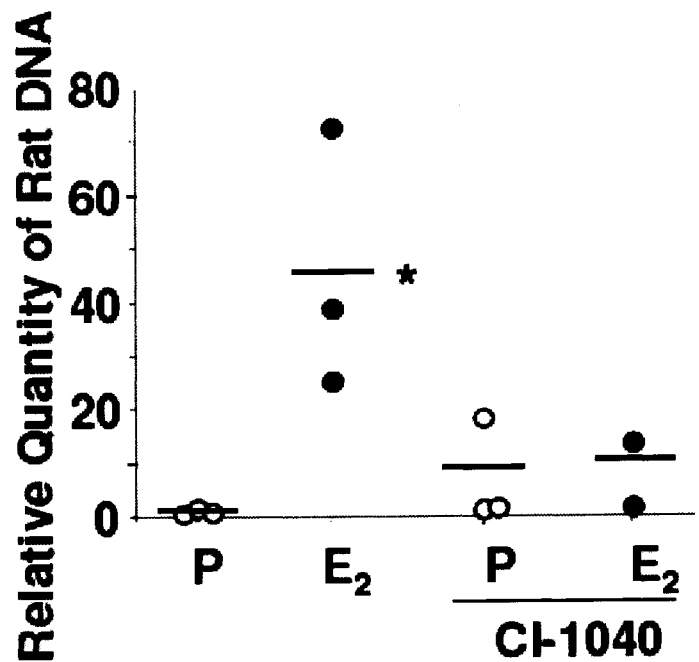
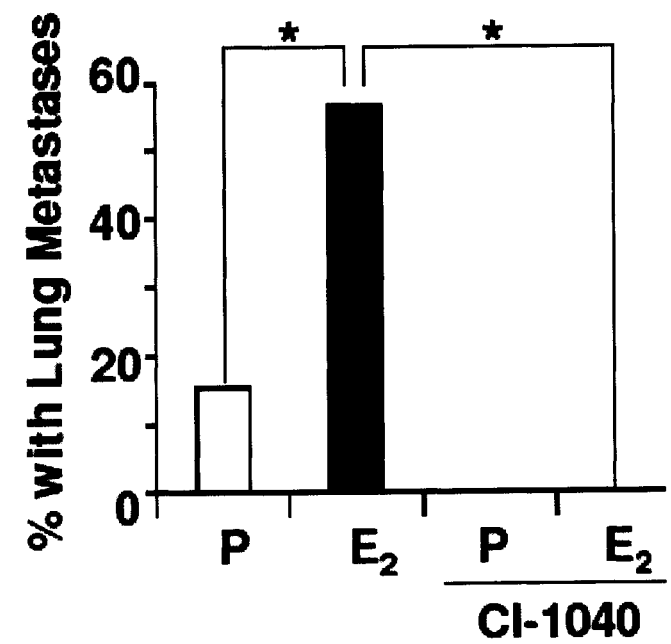

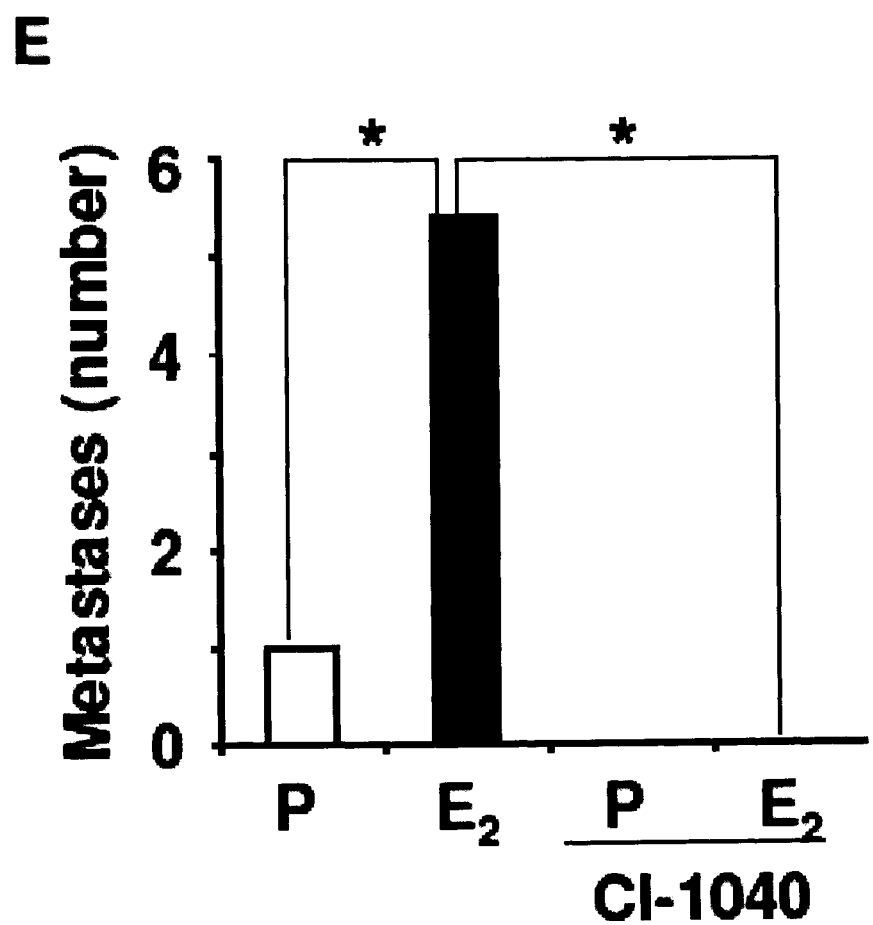
Fig. 6 –cont'd

METHOD FOR THE TREATMENT OF LYMPHANGIOLEIOMYOMATOSIS (LAM)

CROSS-REFERENCE TO RELATED APPLICATIONS

The present application is the U.S. National Stage of International Application No. PCT/US09/44643, filed May 20, 2009, which claims the benefit of U.S. Provisional Patent Application No. 61/054,714, filed May 20, 2008, the entire disclosure of which is incorporated by reference herein.

STATEMENT REGARDING FEDERAL SPONSORED RESEARCH OR DEVELOPMENT

The present invention was made with funds provided by the National Institute of Health under Grant No. HL 60746. The U.S. Government has certain rights in this invention.

FIELD OF THE INVENTION

The present invention relates to the treatment or prophylaxis of lymphangioleiomyomatosis (LAM) in mammals, by the administration of certain inhibitors of the dual-specificity kinases MEK-1 and MEK-2, as well as a novel animal model useful in the development of potential targeted therapies for LAM and other estrogen-mediated malignancies.

BACKGROUND OF THE INVENTION

LAM, the pulmonary manifestation of tuberous sclerosis complex (TSC), is an often-fatal disease which is characterized by the widespread proliferation of abnormal smooth muscle cells that grow aberrantly in the lung, producing cystic changes within the lung parenchyma (Sullivan, E. J., Chest, 114: 1689-1703 (1998)). For reasons that are not clearly understood, LAM affects women almost exclusively. LAM affects 30-40% of women with TSC (Costello, L. C. et al., Mayo Clin. Proc. 75: 591-594 (2000); Franz, D. N. et al., Am. J. Respir. Crit. Care Med., 164: 661-668 (2001)). LAM can also occur, in women who do not have clinical manifestations of TSC, as well as those who do not have germline mutations in TSC1 or TSC2 (sporadic LAM).

The lungs in LAM are diffusely infiltrated by histologically benign, immature-appearing smooth muscle cells that express estrogen receptor (ER) alpha and progesterone receptor. This cellular infiltration is accompanied by cystic lung degeneration. Most women with TSC-associated LAM and 60% of women with sporadic LAM have renal angiomyolipomas (AMLs), which contain abnormal smooth muscle cells that are virtually identical to LAM cells. The relentless growth of LAM cells in the pulmonary airway, parenchyma, lymphatics and blood vessels leads to respiratory failure and death. In a Mayo Clinic series, LAM was the third most frequent cause of TSC-related death, after renal disease and brain tumors (Shepherd, C. W. et al., Mayo Clin. Proc., 66: 792-796 (1991)).

Genetic studies by the present inventors and others have revealed that LAM cells from both TSC-LAM and sporadic LAM carry inactivating mutations in both alleles of the TSC1 or TSC2 genes, and spread to the lungs via a metastatic mechanism despite the fact that LAM cells have a histologically benign appearance. Genetic evidence for this "benign metastasis" model of LAM has arisen from women with the sporadic form of LAM, who have somatic TSC2 mutations in LAM cells and renal AML cells but not in normal kidney, lung, or peripheral blood cells (Yu, J. et al., Am. J. Respir. Crit. Care Med., 164: 1537-1540 (2001); Carsillo, T., Proc. Natl. Acad. Sci. USA, 97: 6085-6090 (2000)); and fluorescent in situ hybridization analysis of LAM that recurs after lung transplantation (Karbowniczek, M. et al., Am. J. Respir. Crit. Care Med., 167: 976-982 (2003)). The presence of disseminated neoplastic cells has been detected in blood and body fluids from LAM patients (Crooks, D. M. et al., Proc. Natl. Acad. Sci. USA, 101: 17462-17467 (2004)).

The protein products of TSC1 and TSC2, hamartin and tuberin, respectively, form heterodimers (Plank, T. L. et al., Cancer Res., 58: 4766-4770 (1998); van Slegtenhorst, M. et al., Hum. Mol. Genetc., 7: 1053-1057 (1998)) that inhibit the small GTPase Ras homologue enriched in brain (Rheb), via tuberin's highly conserved GTPase activating domain. In its active form, Rheb activates the mammalian target of rapamycin (mTOR) complex 1 (TORC1), which is a key regulator of protein translation, cell size, and cell proliferation (Crino, P. B., N. Engl. J. Med., 355: 1345-1356 (2006). Evidence of OTRC1 activation, including hyperphosphorylation of ribosomal protein S6, has been observed in tumor specimens from TSC patients and LAM patients (El-Hashemite, N. et al., Lancet, 361: 1348-1349 (2003); Karbowniczek, M. et al., Am. J. Pathol., 162: 491-500 (2003); Yu, J., Am. J. Physiol. Lung Cell Mol. Physiol., 286: L694-700 (2004)). Independent of its activation of mTOR, Rheb inhibits the activity of B-Raf and C-Raf/Raf-1 kinase, resulting in reduced phosphorylation of p42/44 MAPK (Im. E. et al., Oncogene, 21: 6356-6365 (2002); Karbowniczek, M. et al., J. Biol. Chem., 279: 29930-29937 (2004); Karbowniczek, M. et al., J. Biol. Chem., 281: 25447-25456 (2006)), but the impact of the Raf/MEK/MAPK pathway on disease pathogenesis is undefined.

The female predominance of LAM, coupled with the genetic data indicating that LAM cells are metastatic, suggests that estrogen may promote the metastasis of tuberin-null cells. Both LAM cells and angiomyolipoma cells express estrogen receptor alpha (Logginidou, H. et al., Chest., 117: 25-30 (2000)), and there are reports of symptom mitigation in LAM patients after oophorectomy and worsening of symptoms during pregnancy (Sullivan, E. J. et al., supra). However, the molecular and cellular mechanisms that may underlie an impact of estrogen on the metastasis of LAM cells are not well defined, in part because of the lack of in vivo models that recapitulate the metastatic behavior of LAM cells.

Oxygen therapy may become necessary if the disease continues to worsen and lung function is impaired. Lung transplantation is considered as a last resort.

Although the immunosuppressant drug sirolimus (rapamycin) has shown preliminary promise as a potential LAM therapy, there is no currently approved drug for the treatment or prophylaxis of LAM.

New therapies and preventatives are clearly needed for LAM and related pathologies of similar etiology.

SUMMARY OF THE INVENTION

In accordance with one aspect of the present invention, there is provided a method for the treatment or prophylaxis of lymphangioleiomyomatosis (LAM) comprising administering to a patient in need of such treatment or prophylaxis a therapeutically effective amount of a compound having the formula:

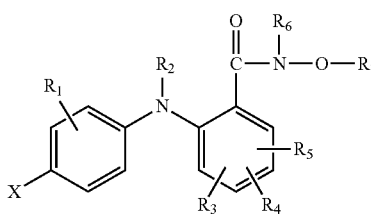

wherein:

$R_1$ is hydrogen, hydroxy, $C_1$-$C_8$ alkyl, $C_1$-$C_8$ alkoxy, halo, trifluoromethyl, or CN;

$R_2$ is hydrogen;

$R_3$, $R_4$, and $R_5$ independently are hydrogen, hydroxy, halo, trifluoromethyl, $C_1$-$C_8$ alkyl, $C_1$-$C_8$ alkoxy, nitro, CN, or (O or NH)$_m$—(CH$_2$)$_n$—$R_9$, where $R_9$ is hydrogen, hydroxy, CO$_2$H or NR$_{10}$R$_{11}$;

n is 0 to 4;

m is 0 or 1;

$R_{10}$ or $R_{11}$ independently are hydrogen or $C_1$-$C_8$ alkyl, or taken together with the nitrogen to which they are attached can complete a 3- to 10-member cyclic ring optionally containing one, two, or three additional heteroatoms selected from O, S, NH, or N—$C_1$-$C_8$ alkyl;

$R_6$ is hydrogen, $C_1$-$C_8$ alkyl,

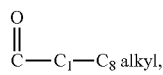

aryl, aralkyl, or $C_3$-$C_{10}$ cycloalkyl;

$R_7$ is hydrogen, $C_1$-$C_8$ alkyl, $C_2$-$C_8$ alkenyl, $C_2$-$C_8$ alkynyl, $C_3$-$C_{10}$ (cycloalkyl or cycloalkyl optionally containing a heteroatom selected from O, S, or NR$_9$);

X is bromine or iodine;

and wherein any of the foregoing alkyl, alkenyl, and alkynyl groups can be unsubstituted or substituted by cycloalkyl (or cycloalkyl optionally containing a heteroatom selected from O, S, or NR$_9$), aryl, aryloxy, heteroaryl, or heteroaryloxy; or $R_6$ and $R_7$ taken together with the N—O to which they are attached can complete a 5- to 10-membered cyclic ring, optionally containing one, two, or three additional heteroatoms selected from O, S, or NR$_{10}$R$_{11}$.

In another aspect, the present invention provides a xenograft rodent model using TSC2-deficient rat uterine lecomyoma (ELT3) cells, which upon subcutaneous inoculation into CB17-scid mice and subsequent administration of estrogen, develop tumors and exhibit pulmonary metastases. This animal model serves as a useful tool for the identification of agents having therapeutic efficacy for the treatment of LAM, and other hormonally-driven conditions.

As will appear in the following description, the research underlying this invention revealed that the MEK pathway is a critical component of the estrogen-dependent metastatic potential of Tsc2-null cells, and lead to a unique model of LAM pathogenesis with therapeutic implications in which $E_2$ promotes the survival of disseminated LAM cells, thereby facilitating lung colonization and metastasis. See Yu, J. J. et al., PNAS, 106(8): 2635-2640 (2009)

BRIEF DESCRIPTION OF THE DRAWINGS

FIG. 1A—The proliferation of ELT3 cells in response to E2 was measured by 3H-thymidine incorporation after 5 days of growth;

FIG. 1B—Lung metastases were scored from E2 (n=9) or placebo-treated (n=10) mice;

FIG. 1C—The number of lung metastases in male mice was scored from placebo (n=10) and E2-treated (n=9) mice;

FIG. 1D-FIG. F—Consecutive lung sections containing metastases (arrows) from an E2-treated female mouse were stained with hematoxylin and eosin (H&D) (FIG. 1D); anti-smooth muscle actin (FIG. 1E); and anti-phospho-S6 (FIG. 1F) (scale bar, 50 μM)

FIG. 1G—Anti-phospho-S6 immunostain of the primary xenograft tumor of an estrogen-treated female mouse.

FIG. 1H—Phospho-S6 immunoreactivity of a metastasis of an estrogen-treated male mouse;

FIG. 1I—Phospho-S6 immunoreactivity of a xenograft tumor of an estrogen-treated male mouse (scale bar, 20 μM).

FIG. 2A—DNA prepared from the blood of placebo (n=3) and $E_2$-treated (n=3) mice bearing xenograft tumors of similar size (≈1,000 mm$^3$) was analyzed by real-time PCR using rat-specific primers to quantitate circulating tumors;

FIG. 2B—Levels of circulating tumor cell DNA 6 h after i.v. injection of ELT3 cells into placebo (n=3) and $E_2$-treated (n=3) mice; and FIG. 2C—Levels of tumor cell DNA in the lungs 24 h after i.v. injection of ELT3 cells into placebo (n=3) and $E_2$-treated (n=3) mice.

FIG. 3A—ELT3-luciferase cells were injected intravenously into overiectomized female placebo (n=3) and $E_2$-treated (n=3) mice. Lung colonization was measured using bioluminescence at 1, 3, and 24 h after injection. Representative images are shown;

FIG. 3B—Total photon flux/second present in the chest regions in placebo (n=3) and $E_2$-treated (n=3) animals.

FIG. 3C—Lungs were dissected 24 h postcell injection and bioluminescence was imaged in Petri dishes.

FIG. 4A—Levels of phosphorylated p42/44 MAPK and total MAPK were determined by immunoblot analysis. Pretreatment with PD98059 blocked $E_2$-induced MAPK activation. 13-Actin immunoblotting was included as a loading control;

FIG. 4B—Levels of phosphorylated C-Raf/Raf-1 and total Raf-1 after $E_2$ stimulation;

FIG. 4C—Levels of phosphorylated S6 after E2 stimulation;

FIG. 4D—The nuclear and cytoplasmic fractions were separated, and levels of phosphor-p42/44 MAPK were examined by immunoblot analysis. Anti-ELK1 and anti-α-tubulin were included as loading controls for the nuclear and cytosolic fractions, respectively;

FIG. 4E-FIG. 4F—Pulmonary metastases from an $E_2$-treated mouse showed hyperphosphorylation of p42/44 MAPK (scale bar, 50 μM and 125 μM);

FIG. 4G-FIG. 4H—Phospho-p42/44 MAPK (T202/Y204) immunostaining of primary tumor sections from placebo-treated mice (FIG. 4G) and E2-treated mice (FIG. 4H); and FIG. 4I—Percentage of cells with nuclear immunoreactivity of phosphor-p42/44 MAPK was scored from 4 random fields per section.

FIG. 5A—The level of cleaved caspase-3 was determined by immunoblot analysis. α-Tubulin is included as a loading control;

FIG. 5B—DNA fragmentation was assessed by ELISA;

FIG. 5C—Cell growth was measured by 3H-thymidine incorporation after 24 h of growth on PolyHEMA plates in the presence or absence of $E_2$, followed by 24 h of growth on adherent plates in the absence of $E_2$; and FIG. 5D—Levels of phosphor-p42/44 MAPK, MAPK, Bim, cleaved caspase-3, phosphor-S6K, and phosphor-S6 were determined by immunoblot analysis. α-Tubulin is included as a loading control.

In FIG. 6A-FIG. 6E, animals were treated with CI-1040 (150 mg/kg/day by gavage, twice a day) starting 1 day post-ELT3 cell inoculation for the xenograft experiments.

FIG. 6A—Tumor development was recorded as the percentage of tumor-free animals post-cell inoculation;

FIG. 6B—The primary tumor area was calculated at 7 weeks post-cell inoculation;

FIG. 6C—The level of circulating ELT3 cells was measured from blood samples of xenograft animals using rat-specific qPCR amplification;

FIG. 6D—The percentage of mice with lung metastases in the placebo and estrogen-treated groups was compared;

FIG. 6E—The number of lung metastases was scored;

FIG. 6F—ELT3-luciferase cells were injected intravenously into overiectomized female $E_2$-treated (n=5) and CI-1040 plus $E_2$-treated (n=5) mice. CI-1040 was administered according to the same regimen starting 2 days before cell inoculation. Lung colonization was measured using bioluminescence 2 and 5 h after injection. Total photon flux/second present in the chest regions were quantified and compared between $E_2$ (n=5) and CI-1040 plus $E_2$-treated (n=5) animals. Lungs were dissected and imaged 60 h post-cell injection. Total photon flux/second present in ex vivo lungs were quantified and compared between $E_2$ (n=5) and CI-1040 plus $E_2$-treated (n=5) animals.

In FIG. 7A, the primary tumor area was calculated at 8 weeks post-cell inoculation. In FIG. 7B, the number of lung metastases was scored at 8 weeks post-cell inoculation. *, P<0.05, Student's t test.

DETAILED DESCRIPTION OF THE INVENTION

Figure 1:
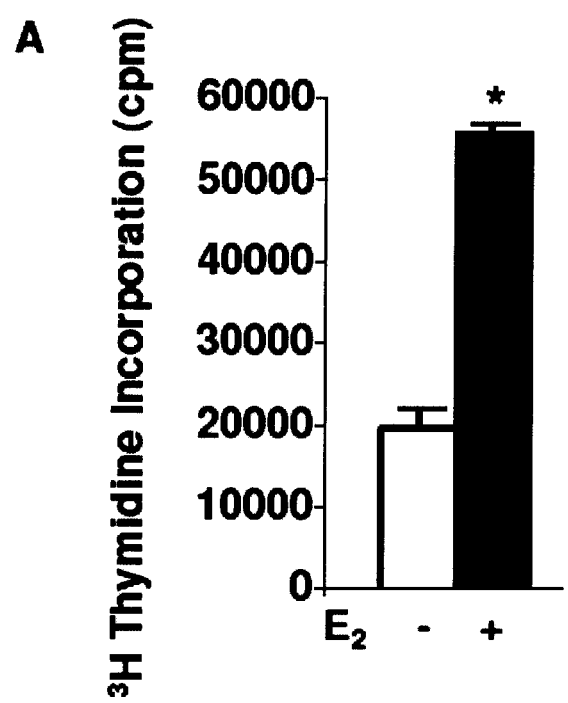
FIG. 1 shows the results of various experiments indicating that estrogen promotes the lung metastasis of tuberin-deficient ELT3 cells in female and male mice, including.
Figure 1:
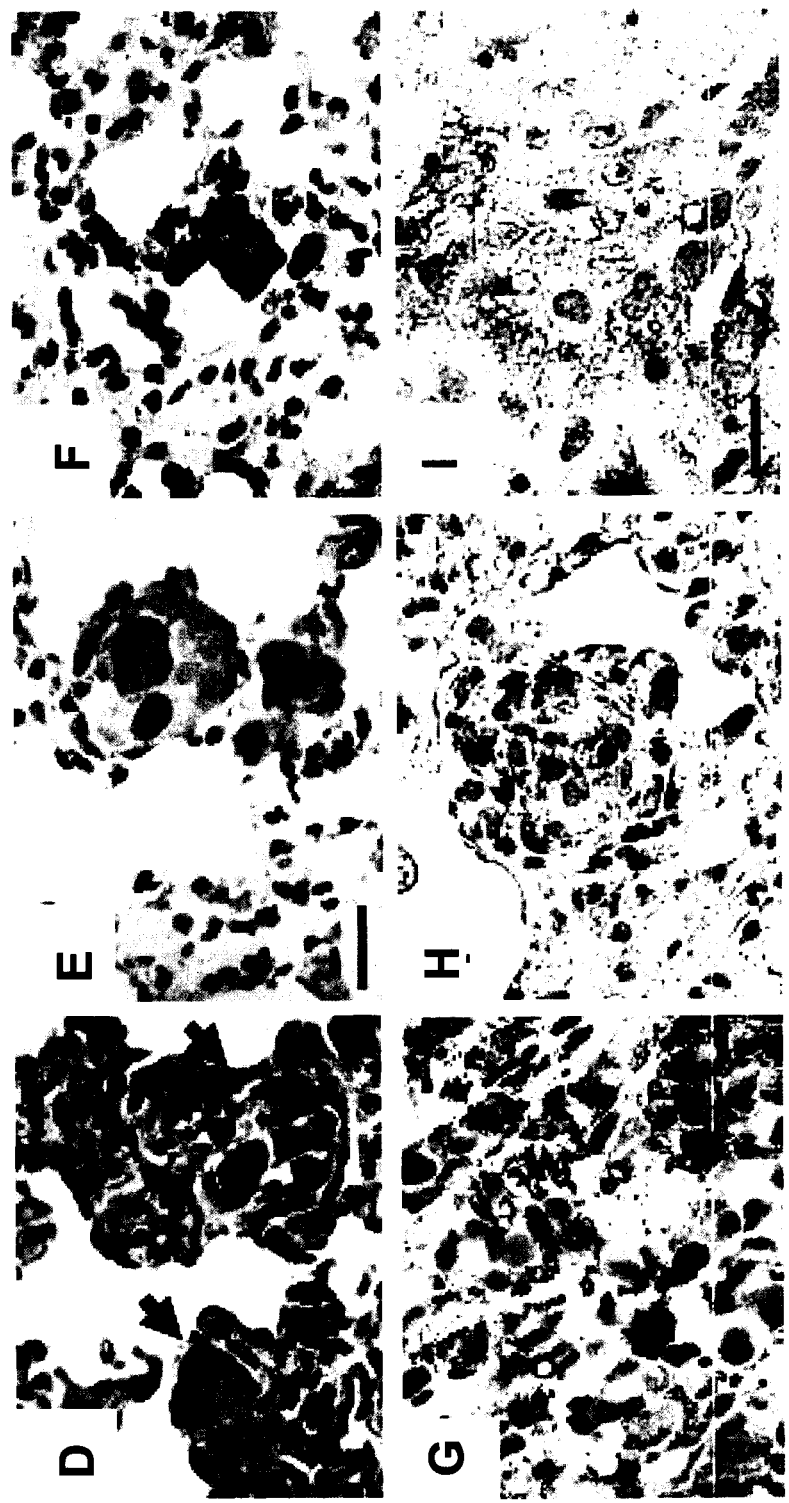

The present invention is based, in part, on important insights gained from the discovery that 17β-estriadiol (E2) promotes the pulmonary metastases of tuberin-deficient ELT3 cells, associated with activation of p42/44 mitogen-activated protein kinase (MAPK), elevated number of circulating tumor cells and prolonged survival of intravenously injected ELT3 cells. In other words, estrogen was found to induce the dissemination of tumor cells, increase the number of circulating tumor cells and enhance lung colonization. This discovery suggested several regimens for possible therapeutic intervention against LAM, including treatment with an inhibitor of the dual specificity kinases, MEK-1 and MEK-2. The latter approach was found to delay the development of primary tumors and block estrogen-induced lung metastases in animals. Inhibition of MEK1/2 also reduced the number of circulating ELT3 cells and decreased their lung colonization after intravenous injection.

The MEK1/2 inhibitor that produced these results, namely, 2-(2-chloro-4-iodo-phenylamino)-N-cyclopropylmethoxy-3,4-difluoro-benzamide (also known as CI-1040), is from a class of compounds referred to as phenylamino-benzhydroxamic acid derivatives, which are represented by Formula I, above.

In view of the mechanism of action of CI-1040, i.e., inhibition of the mitogen activated extracellular signal regulated kinase (ERK) pathway which is known to be involved in key cellular activities including proliferation, differentiation, apoptosis and angiogenesis, it is believed that analogous compounds within the scope of Formula I, above, will exhibit similar therapeutic activity against LAM.

The synthesis of phenylamino-benzhydroxamic acid derivatives of Formula I, above, and the preparation of pharmaceutical compositions comprising such derivatives are described in detail in International Patent Application No. PCT/US98/13106 (WO 99/01426) and U.S. Pat. No. 6,821,963.

A suitable route of administration and maximum tolerable dose for administration of CI-1040 to humans have been determined in a phase I and pharmacodynamic study (LoRusso (2005)).

The therapy described herein will typically be administered for a period of time sufficient to provide an appreciable improvement or stabilization of lung function in the patient undergoing treatment, as determined by a reduction in lung metastasis and/or a reduction in tumor burden. As used herein, the term "patient" refers to animals, including mammals, preferably humans.

The term "anoikis" as used herein refers to matrix deprivation-induced apoptosis which is a form of programmed cell death induced when anchorage-dependent cells detach from the surrounding extracellular matrix (ECM). The ECM provides essential signals for cell growth or survival. When cells are detached from the ECM, i.e. there is a loss of normal cell-matrix interactions, they may undergo anoikis. Metastatic tumor cells are often resistant to anoikis and invade other organs.

While not wishing to be confined to any particular theory regarding the mechanism responsible for the observed therapeutic effect that the compounds of Formula I have on LAM, it is believed that the compounds disrupt key signaling events associated with angiogenesis and cellular proliferation.

Based on the suspected mechanism of action of the compounds of Formula I, as mentioned above, it is anticipated that these compounds will be useful not only for therapeutic treatment of LAM, but for prophylactic use as well. The dosages may be essentially the same, whether for treatment or prophylaxis of LAM.

Applications of the compounds described herein may extend to other estrogen-mediated malignancies by modulating MEK/MAPK signalling. It has been shown, for example, that estrogen enhances liver hemangioma development in Tsc±mice (El-Hashemite et al., Cancer Res., 65: 2474-2481 (2005)).

The following examples describe the invention in further detail. These examples are provided for illustrative purposes only and should in no way be construed as limiting the invention.

Materials and Methods

Cell Culture and Reagents

ELT-3 cells (Eker rat uterine leiomyoma-derived smooth muscle cells) were cultured in IIA complete medium (DMEM/F12 basal media including 15% FBS, 0.2 μM hydrocortisone, 10 μU/mL vasopressin, 1×FeSO4, 10 ng/mL EGF, 1×ITS, 0.01 nM triiolythryonine, 0.12% sodium bicarbonate, 1× cholesterol and 1× penicillin/streptomycin) supplemented with 15% FBS. Prior to the in vitro experiments, cells were maintained in media supplemented with 10%-charcoal-stripped FBS for three days and then serum starved for 24 hours in serum-free and phenol red-free medium. E2 (10 nM, Sigma, St. Louis, Mo.) or PD98059 (50 μM, Cell Signaling Technology, Danvers, Mass.) was added to the cells as indicated.

Immunoblotting and Antibodies

Cells were rinsed once in ice-cold PBS and lysed in PTY buffer (50 mM Hepes, pH 7.5, 50 mM NaCl, 5 mM EDTA, 50 mM NaF, 10 mM $Na_4P_2O_7$, and 1% Triton 100) supplemented with phosphatase inhibitors. Lysates were resolved by SDS-PAGE electrophoresis and transferred onto Immobilon P membranes (Millipore). Cytoplasmic and nuclear fractions were separated using CellLytic Nuclear Extraction Kit (Sigma) before electrophoresis. The following antibodies were used for Western blot analysis: anti-Bim (Affinity BioReagents), anti-S6, anti-phospho-S6 (S235/236), anti-phospho-S6K (T389), anti-phospho-p42/44 MAPK (T202/Y204), anti-p42/44MAPK, anti-ELK1, anti-cleaved caspase 3 (all from Cell Signaling technology), anti-Ki67 and antismooth muscle actin (Bio-Genex), anti-alpha-tubulin and anti-beta-actin (Sigma), anti-phospho-Raf-1 (S338) (Upstate Biotechnology), and anti-Raf-1 (Santa Cruz Biotechnology). Western blots were developed using horseradish peroxidase-conjugated secondary antibodies and ECL chemiluminescence (Amersham Biosciences).

Immunohistochemistry

Sections were deparaffinized, incubated overnight with primary antibodies at 4° C. in a humidified chamber and then rinsed and incubated with biotinylated secondary antibodies for 30 minutes at room temperature. Slides were developed using the Broad Spectrum AEC Histostain-Plus (Invitrogen) or Histostain-Plus kit (Invitrogen), and they were counterstained with Gill's hematoxylin.

Animal Studies

All animal work was performed in accordance with a protocol approved by the FCCC Institutional Animal Care and Use Committee. Male CB-17 scid mice, six weeks of age, were purchased from Fox Chase Cancer Center. Female ovariectomized CB17-scid mice, six to eight weeks of age, were purchased from Taconic (Hudson, N.Y.). One week prior to cell injection, 17-beta estradiol or control-placebo pellets (2.5 mg, 90-day release) (Innovative Research America, Sarasota, Fla.) were implanted. For xenograft tumor establishment, subconfluent ELT3 cells were harvested, washed in PBS, and resuspended in 0.2 ml of serum-free medium. Two millions ELT3 cells were injected into both flanks of the mouse subcutaneously. For metastatic and circulating tumor cells assays, 2×105 ELT3 or ELT3-Luc cells were resuspended in 0.1 ml PBS and injected into the lateral tail vein of mice. Lung metastases were scored from 3-5 five-micron H&E stained sections of each lobe at 40× magnification by observers blinded to the experimental conditions.

Pharmacological Inhibitor

CI-1040 (PD184352) was obtained from Pfizer (Ann Arbor, Mich.) and was prepared in a vehicle of 10% Cremophore EL (Sigma), 10% ethanol and 80% water. RAD001 was obtained from Novartis Pharma AG (Basel, Switzerland) and was diluted in double-distilled water. Drug were administered one day post cell inoculation at the following doses: RAD001 (4 mg/kg/day, gavage); CI-1040, (150 mg/kg/day gavage, twice a day)

Xenograft Tumor Samples

Subcutaneous tumors were removed from animals upon sacrifice. Tumor weights were recorded, and tumor size was measured in two dimensions with calipers.

Detection of ELT Cells by Real-Time PCR

Mouse blood (0.5 mL) was collected at indicated times by intraocular bleed, and red blood cells were lysed before DNA extraction. At death, the lungs were dissected and stored at −80° C. for DNA extraction. Rat and mouse DNAs were quantified by using TaqMan-chemistry based real-time PCR assays. The assay for rat DNA was adapted from the method described by Walker et al., Genomics, 83: 518-527 (2004). The primers amplify a LINE repeat element (AC087102). The assay for mouse is for the gene Anf. The sequences (all 5' to 3') for the primers and probes are:

```
Mouse Forward:
                                      (SEQ ID NO: 1)
GGCATCTTCTGCTGGCTCC;

Reverse:
                                      (SEQ ID NO: 2)
GGCTA GAACCCTCCCCATTCT;

Probe:
                                      (SEQ ID NO: 3)
6FAM-CACTCCATCGCTTATCGCTGCAAGTG-BHQ1.

Rat Forward:
                                      (SEQ ID NO: 4)
CAAGACGGATGATCAAAATGTG;

Reverse:
                                      (SEQ ID NO: 5)
TCTCTGTTTTAATCTTTGCCT CTCC;

Probe:
                                      (SEQ ID NO: 6)
6FAM-CCTGCCAAGGGTATTCTTTTTCCTCATTTAAA-BHQ1.
```

PCR master mix from Eurogentec was used for PCR. Primers and probe concentrations were 500 and 100 nM, respectively. Cycling conditions were 95° C., 15 minutes followed by 40 (2-steps) cycles (95° C., 15 sec; 60° C., 60 sec). Reactions were run using an ABI 7900 HT instrument. Each sample was analyzed using two different amounts of input DNA. Relative quantification was done using the $2^{-\Delta\Delta Ct}$ method (Livak. K. J., Methods, 25: 402-408 (2001)).

Bioluminescent Reporter Imaging

One million ELT3 cells were transfected with 3 μg of pCMV-Luc (Invitrogen, Carlsbad, Calif.) using Nucleofection reagent (Amaxa, Gaithersburg, Md.). Cells were selected in G418 for 2 weeks, and G418 resistant clones were isolated and examined for luciferase activity.

Ten minutes prior to imaging, animals were injected with luciferin (Xenogen, Alameda, Calif.) (120 mg/kg, i.p.). Bioluminescent signals were recorded at indicated times post cell injection using Xenogen IVIS System (Xenogen). Total photon flux at the chest regions and from the dissected lungs was analyzed.

Anoikis Assay

ELT3 cells were cultured with or without 10 nM $E_2$ in serum-free and phenol red-free medium supplemented with 10% charcoal-stripped FBS for 24 hours. Cells were harvested, plated onto 60×15 mm style Poly-hydroxyethyl methacrylate (PolyHEMA) culture dishes (Corning Incorporated) at a density of 1×606 cells/mL with or without $E_2$. Cell death as a function of DNA fragmentation was detected using Cell Death Detection ELISA kit (Roche Diagnostics).

Thymidine Incorporation

The surviving cells in suspension were plated in triplicate in 24-well plates and allowed to grow adherently for 24 hours. $^3$H-thymidine (1 µCi) was added to the media and the cells were incubated at 37° C. for 6 hours, washed with PBS, and lysed in 0.5 mL of 0.5 N NaOH plus 0.5% SDS. $^3$H-thymidine incorporation was measured by scintillation counting.

Statistical Analysis

Statistical analyses were performed using Student's t test when comparing 2 groups. Results are presented as means±SD of experiments performed in triplicate. Differences were considered significant at P<0.05 (*).

Results

Estrogen Promotes Pulmonary Metastasis of Tuberin-Deficient ELT3 Cells in Ovariectomized Female and Male Mice To study the role of $E_2$ in the metastasis of Tsc2-null cells, ELT3 cells were used, which were originally derived from a uterine leiomyoma in the Eker rat model of Tsc2 and, similar to LAM cells, express smooth muscle cell markers and estrogen receptor alpha (Howe et al., Am. J. Pathol., 146: 1568-1579 (1995); Howe, S. R. et al., Endocrinology, 136: 4996-5003 (1995)). To confirm that ELT3 cells proliferate in response to estrogen stimulation in vitro, cell growth was measured using $^3$H-thymidine incorporation. $E_2$ treatment resulted in a significant increase in $^3$H-thymidine incorporation by 2.8-fold on day 5 (P=0.03, FIG. 1A), similar to the findings of Howe et al., Endocrinology, supra (1995)).

ELT3 cells were inoculated subcutaneously into the flanks of ovariectomized CB17-SCID mice, which were supplemented 1 week before with either placebo or $E_2$ pellets (2.5 mg, 90-day release). Tumors arose in 100% of both estrogen and placebo-treated mice. At post-inoculation week 8, estrogen-treated mice had a mean tumor area of 287±43 mm$^2$, whereas placebo-treated mice had a mean tumor area of 130±20 mm$^2$ (P=0.0035), consistent with previous findings (Howe et al., Endocrinology, supra (1995)). The proliferative potential of ELT3 cells in vivo was examined using Ki-67 immunoreactivity. The number of Ki-67 positive cells in estrogen-treated tumors was 17% higher than the number in placebo-treated tumors (P=0.03).

Pulmonary metastases were identified in 5 of 9 $E_2$-treated mice (56%), with an average of 15 metastases/mouse (range 4-37) (FIG. 1B). In contrast, only 1 of 9 placebo-treated mice (10%) developed a single metastasis (P=0.039). To determine whether the enhanced metastasis was directly related to tumor size, a subset of placebo-treated mice (n=4) and estrogen-treated mice (n=4) that developed primary tumors at similar size (209±16 and 198±20 mm$^2$, respectively) was analyzed separately. Three of the estrogen-treated mice developed pulmonary metastases with an average of 6 metastases/mouse, while none of the placebo-treated mice developed metastases.

Next, ELT3 cells were inoculated into male mice. At 8 weeks post-cell inoculation, $E_2$-treated animals developed tumors that were 2.9-fold larger than those in the placebo-treated animals. As in the female mice, $E_2$ significantly enhanced the frequency and the number of pulmonary metastases. At 8 weeks post-inoculation, 10 of 10 (100%) of the $E_2$-treated mice developed metastases, with an average of 14 metastases/mouse (range 5-32). In contrast, 7 of 10 (70%) of the placebo-treated mice developed metastases, with an average of 4 metastases/mouse (range 1-7, P=0.013) (FIG. 1C). As expected, the metastatic and primary tumor cells were immunoreactive for smooth muscle actin and phosphor-ribosomal protein S6 (FIG. 1 D-I).

Figure 7:
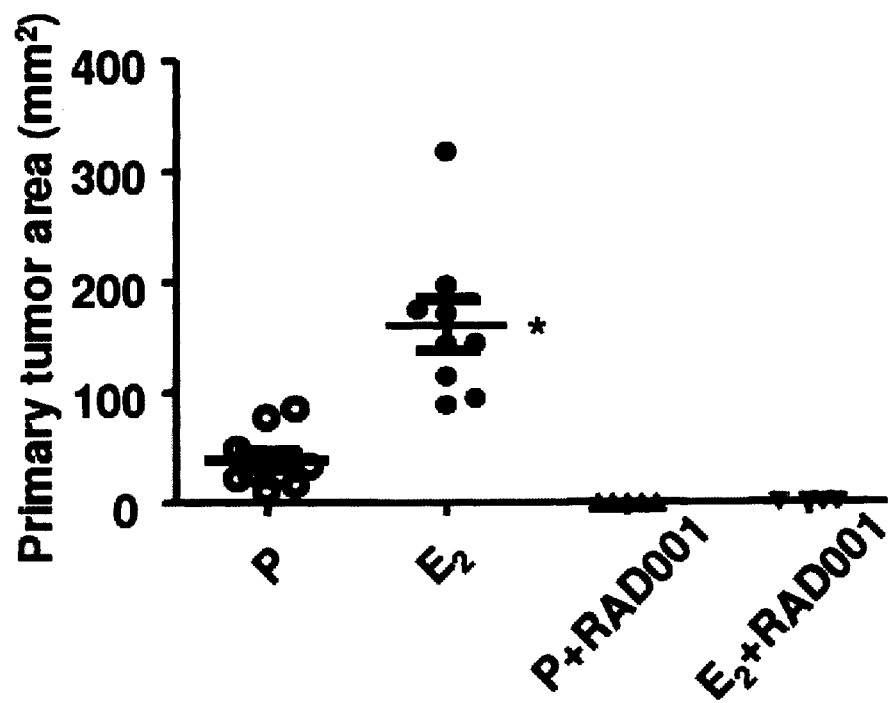
FIG. 7 shows the mTOR inhibitor RAD001 blocks primary tumor development and estrogen-driven metastasis of ELT3 cells in vivo. ELT3 cells were injected into female overiectomized nude mice implanted with estrogen or placebo pellets. Animals were treated with RAD001 (4 mg/kg/day by gavage) starting 1 day post-ELT3 cell inoculation.
Figure 7:
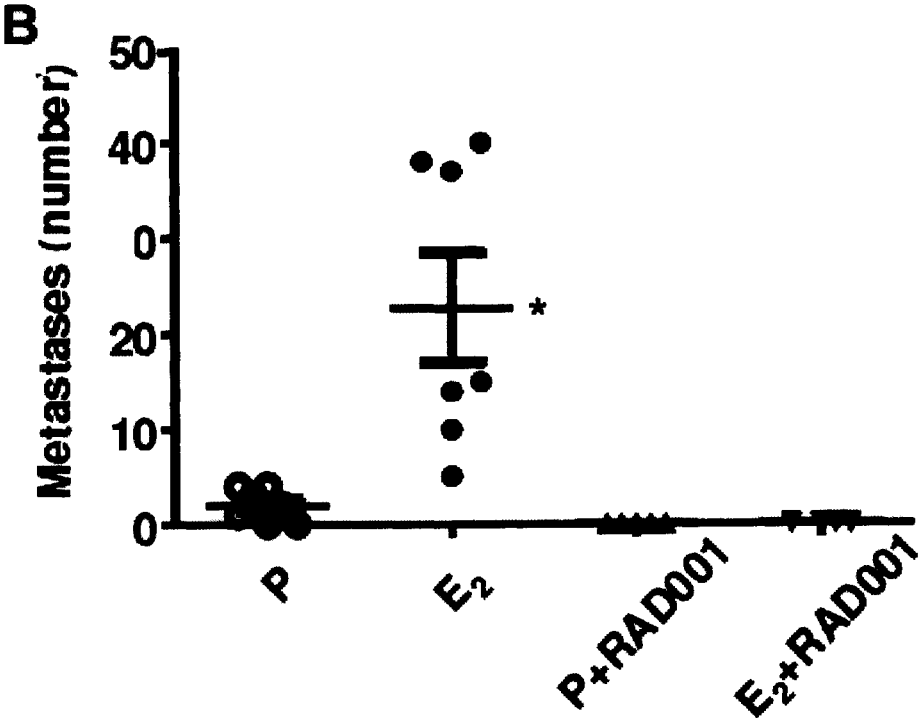

Inhibition of mTOR Blocks Estrogen-Induced Pulmonary Metastasis of Tsc2-Null Cells To determine the role of mTOR signaling pathway in the estrogen-induced metastasis of tuberin-deficient ELT3 cells, the mTORC1 inhibitor RAD001 (4 mg/kg/day by gavage) was administered 5 days per week beginning 1 day post-cell inoculation. RAD001 completely blocked both primary tumor development (FIG. 7A) and lung metastasis (FIG. 7B) in the presence of estrogen or placebo.

Estrogen Increases the Number of Circulating Tumor Cell DNA

Figure 2:
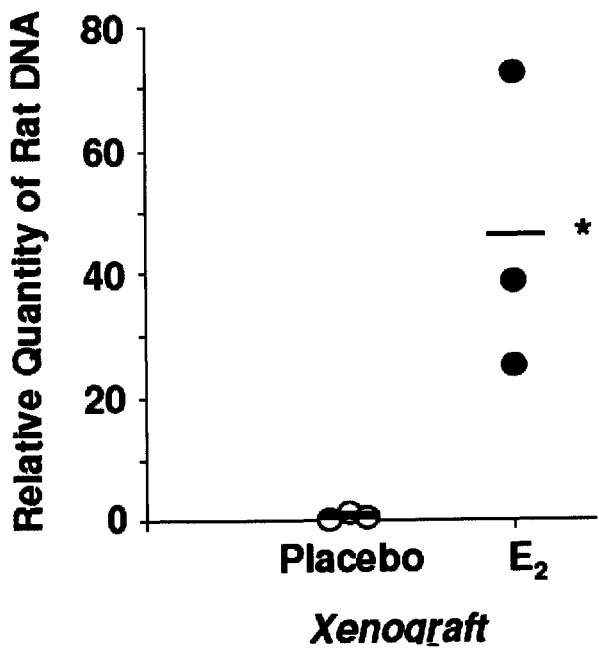
FIG. 2 shows the results of experiments indicating that estrogen increases circulating tumor cells in mice bearing xenograft tumors and enhances the survival and lung seeding of intravenously injected Tsc2-null cells, including.
Figure 2:
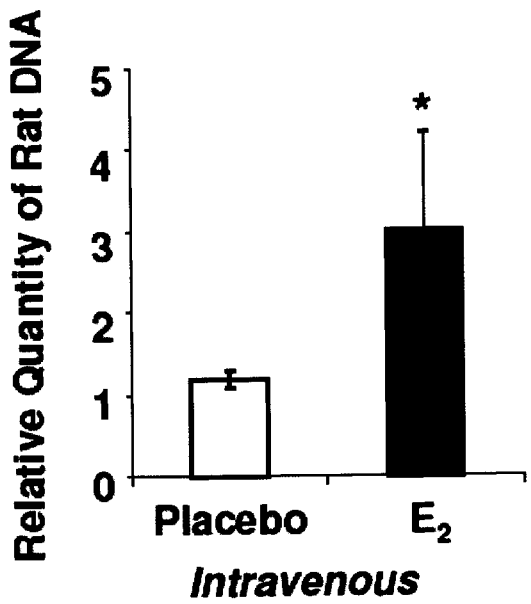

To determine whether the mechanism of $E_2$-driven metastasis of ELT3 cells is associated with an increase in survival of ELT3 cells in the circulation, we analyzed blood collected from xenograft mice at 7 weeks post-cell inoculation. Real-time PCR with rat-specific primers was used to measure the relative quantity of tumor cells circulating in the blood. We selected 6 animals (3 placebo, 3 $E_2$-treated) bearing tumors of similar size (≈1,000 mm$^3$) for this analysis. The $E_2$-treated animals had a striking increase in the amount of circulating tumor cell DNA as compared to that in the placebo-treated animals (P=0.034, FIG. 2A).

This increased level of circulating tumor cell DNA suggested that $E_2$ may promote the survival of Tsc2-null cells upon dissemination from the primary tumor site. To test this, we injected 2×10$^5$ ELT3 cells intravenously and again measured the amount of tumor cell DNA using real-time PCR. $E_2$ treatment results in a 2.5-fold increase in circulating cells 6 h post-injection (P=0.047, FIG. 2B). To determine whether this enhanced survival of circulating cells was associated with increased colonization of the lungs, the mice were killed 24 h after injection, and the lungs were analyzed by real-time PCR. $E_2$ treated mice had a 2-fold increase in the lung seeding of ELT3 cells (P=0.039, FIG. 2C).

Estrogen Promotes the Lung Colonization of ELT3 Cells In Vivo

Figure 3:
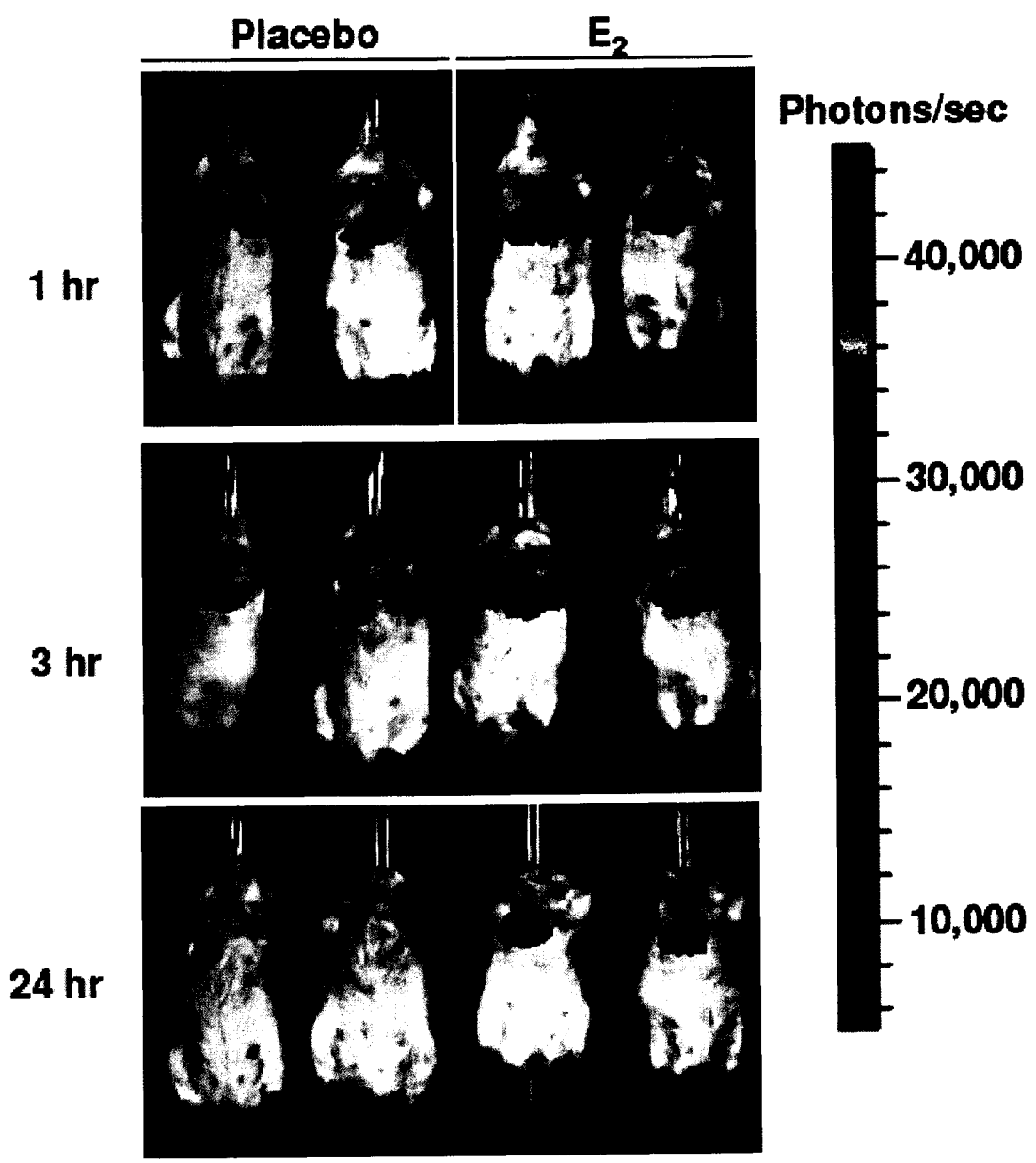
FIG. 3 shows the results of experiments indicating that estrogen promotes the lung colonization of Tsc2-null ELT3 cells, including.

To identify the earliest time points at which estrogen exerts an effect on the survival of intravenously injected Tsc2-null cells, ELT3 cells that stably express luciferase (ELT3-Luc) were intravenously injected. The level of bioluminescence was evaluated using the Xenogen IVIS System. at 1 h post-cell injection, similar levels of bioluminescence were observed in the chest regions of E2 and placebo-treated mice. by 3 h, the bioluminescence in the chest regions was 2-fold higher in the E2-treated animals than in the placebo-treated animals, and at 24 h post-cell injection it was 5-fold higher in the E2-treated animals (P=0.043, FIGS. 3A and B). After sacrifice, the lungs were dissected and imaged in Petri dishes to confirm that the bioluminescent signals in the chest regions of the living mice were a result of lung colonization (FIG. 3C).

Estrogen Activates p42/44 MAPK in ELT3 Cells In Vivo and In Vitro

Figure 4:
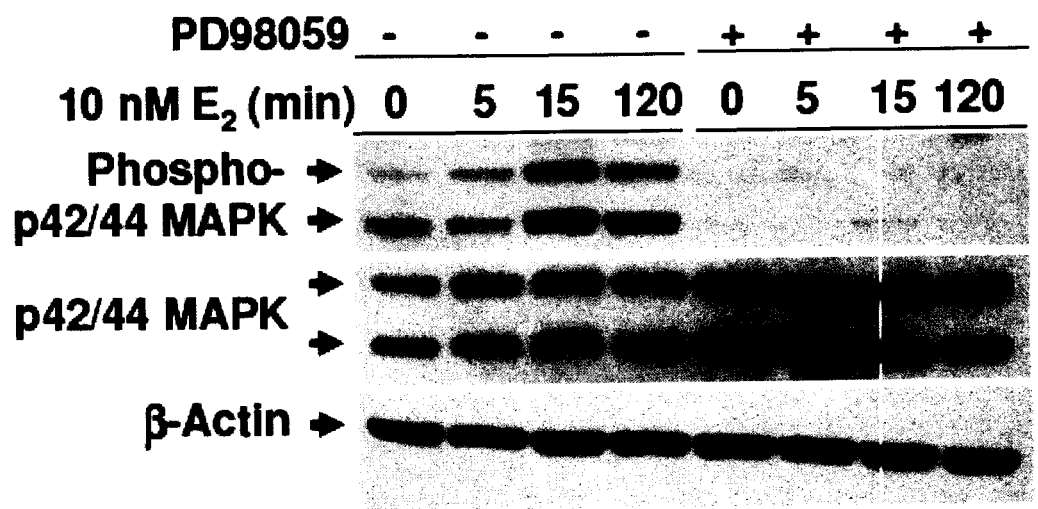
FIG. 4 shows the results of experiments indicating that estrogen activated p42/44 MAPK in ELT3 cells in vitro and in vivo, including.
Figure 4:

These results suggested that $E_2$ promotes the survival of disseminated ELT3 cells. To determine the mechanism of this, we focused on the Raf/MEK/MAPK signaling cascade. This pathway is inhibited in cells lacking TSC2 via Rheb's inhibition of B-Raf and C-Raf/Raf-1 kinase (13, 14). $E_2$ has been shown to activate p42/44 MAPK in ELT3 cells and in LAM patient-derived cells (Yu, J. et al., supra (2004); Finlay, G. A. et al., Am. J. Physiol. Cell Physiol., 285: C409-418 (2003); Finlay, G. A. et al., J. Biol. Chem., 279: 23114-23122 (2004)). To confirm that $E_2$ activated MAPK in ELT3 cells, cells were treated with 10 nM $E_2$ and examined the phosphorylation status of p42/44 MAPK by immunoblotting. Within 15 min, $E_2$ induced the phosphorylation of p42/44 MAPK (FIG. 4A). It was also found that $E_2$-induced phosphorylation of p42/44 MAPK was blocked by the MEK1/2 inhibitor PD98059 (FIG. 4A), which is in contrast to the prior work of Finlay et al., supra. $E_2$ is known to rapidly activate C-Raf (Pratt, M. A. et al., Mol. Cell Biochem, 189: 119-125 (1998)). It was hypothesized that $E_2$ reactivates MAPK via a Rheb-independent pathway in cells lacking tuberin. In a separate experiment, it was found that $E_2$ rapidly (within 2 min) increased the phosphorylation of C-Raf at Ser-338, a site which is closely linked with C-Raf activity (FIG. 4B). However, $E_2$ does not affect mTOR activation as measured by ribosomal protein S6 phosphorylation (FIG. 4C). These results suggest that $E_2$ does not regulate Rheb activity and that the potential of $E_2$ to impact the Raf/MEK/ERK kinase cascade is Rheb independent. Nuclear translocation of phospho-MAPK was observed within 5 min of $E_2$ exposure (FIG. 4D).

These in vitro findings led us to examine whether $E_2$ activates P42/44 MAPK in ELT3 cells in vivo. In lungs from $E_2$-treated animals, nuclear phosphor-p42/44 MAPK staining was observed in metastases but not in adjacent normal tissues (FIGS. 4E and F). In the primary xenograft tumors, the percentage of cells with primarily nuclear phospho-MAPK was significantly higher in the tumors from the $E_2$-treated animals, compared to the tumors from placebo-treated animals (65% vs. 28%, P=0.001, FIG. 4G-I).

Estrogen Increases the Resistance of ELT3 Cells to Anoikis In Vitro

Figure 5:
FIG. 5 shows the results of experiments indicating that estrogen increases the resistance of ELT3 cells to anoikis, including.
Figure 5:
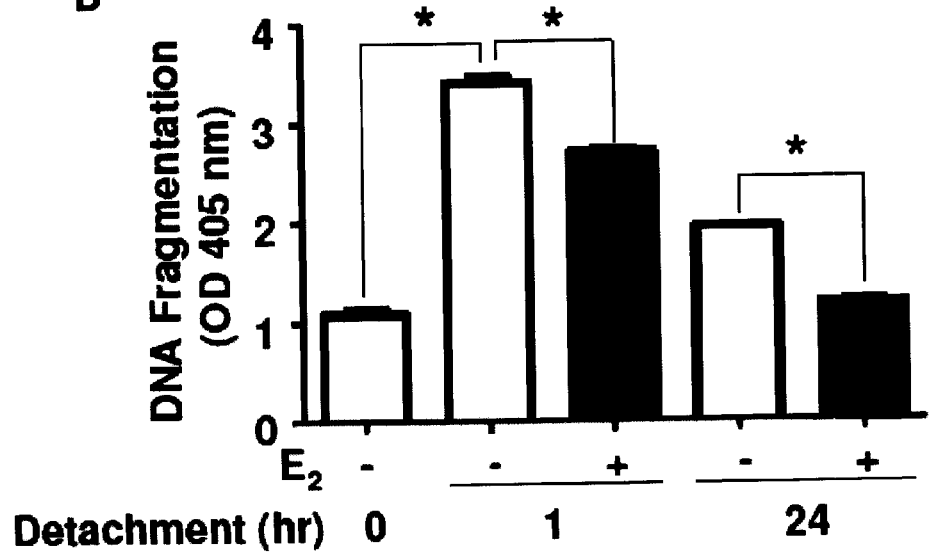
Figure 5:
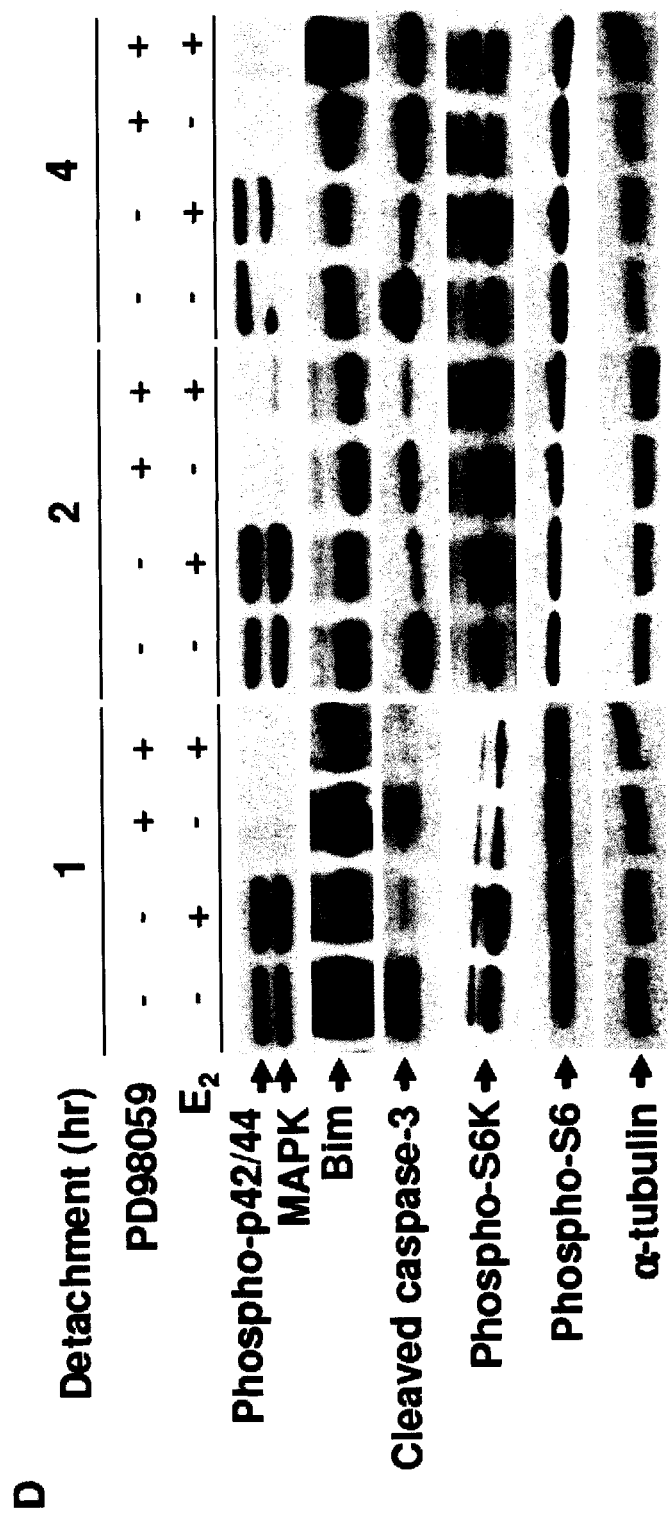

These in vivo findings suggest that estrogen enhances the survival of circulating tumor cells in a MAPK-dependent manner. Because detached cells normally undergo apoptosis (Reginato, M. J. et al., Nat. Cell Biol., 5: 733-740 (2003); Rytomaa, M. et al., Curr. Biol. 9: 1043-1046 (1999); Schulze, A. et al., Genes Dev., 15: 981-994 (2001)), a critical first step in cancer progression is the development of resistance to matrix deprivation-induced apoptosis (anoikis) (Hanahan, D. et al., Cell, 100: 57-70 (2000); Eckert, L. B. et al., Cancer Res., 64: 4585-4592 (2004)). Therefore, to investigate the mechanism of $E_2$-prolonged survival of ELT3 cells in the circulation, we examined the effect of estrogen on anoikis. ELT3 cells were treated for 24 h with either 10 nM $E_2$ or control and then plated onto PolyHEMA, which prevents attachment and therefore induces anoikis. Cell lysates were immunoblotted for cleaved caspase-3, which is a measure of apoptosis. $E_2$ treatment reduced caspase-3 cleavage at 6, 16 and 24 h (FIG. 5A). $E_2$ treatment also significantly reduced DNA fragmentation at 1 and 24 h (P=0.001 and P=0.015, FIG. 5B), which indicates that E2 inhibits anoikis of Tsc2-null cells.

To confirm further that $E_2$ promotes the survival of detached cells, ELT3 cells were plates onto PolyHEMA plates for 24 h and replated onto normal tissue culture dishes. Cell growth was measured using $^3$H-thymidine incorporation. $E_2$ treatment results in a significant increase in $^3$H-thymidine incorporation 24 h after replating (P=0.008, FIG. 5C). This $E_2$-enhanced survival was blocked by treatment with MEK1/2 inhibitor PD98059 (P=0.035, FIG. 5C).

To determine the components that mediate estrogen-enhanced resistance of ELT3 cells to anoikis, we analyzed the proapoptotic protein, Bcl-2 interacting mediator of cell death (Bim), which is known to be a critical activator of anoikis (Reginato, M. J. et al., supra). Bim is phosphorylated by protein kinases, including p42/44 MAPK, which leads to rapid proteasomal-mediated degradation and increased cell survival (Tan, T. T. et al., Cancer Cell, 7: 227-238 (2005)). Bim protein level was examined by immunoblotting. We found that estrogen decreased the accumulation Bim after 1 h in detachment conditions (FIG. 5D). Preincubation with the MEK inhibitor PD98059 partially blocked estrogen's inhibition of Bim accumulation and capase-3 cleavage after 4 h in detachment conditions (FIG. 5D). We also examined the phosphorylation of S6K and S6 in detachment conditions and found that the phosphorylation of S6K and S6 did not change with $E_2$ stimulation. Interestingly, treatment with PD98059 decreased the phosphorylation of S6K 1 h after detachment (FIG. 5D).

Figure 6:
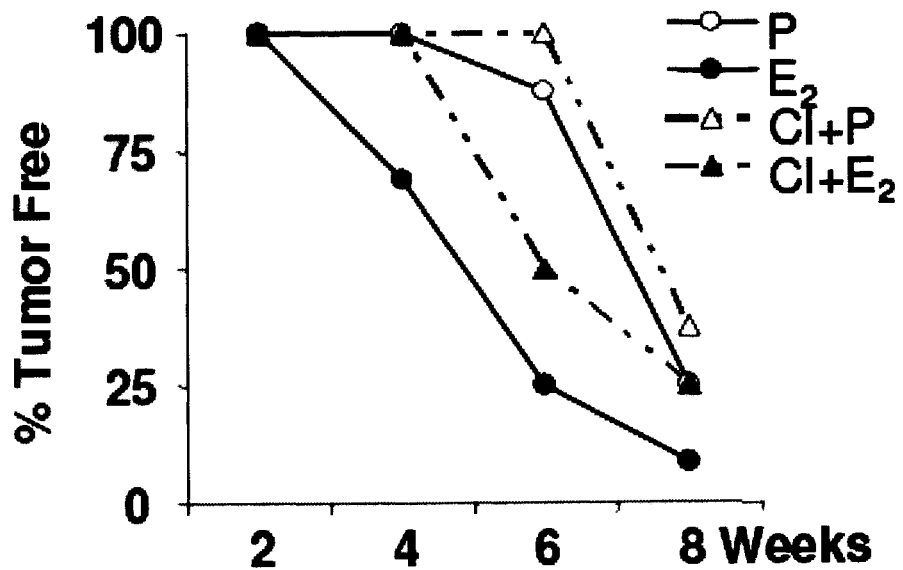
FIG. 6 shows the results of experiments indicating that the MEK 1/2 inhibitor CI-1040 blocks the estrogen driven metastasis of ELT3 cells in vivo. In these experiments, ELT3 cells were injected into female ovariectomized nude mice implanted with estrogen or placebo pellets.
Figure 6:
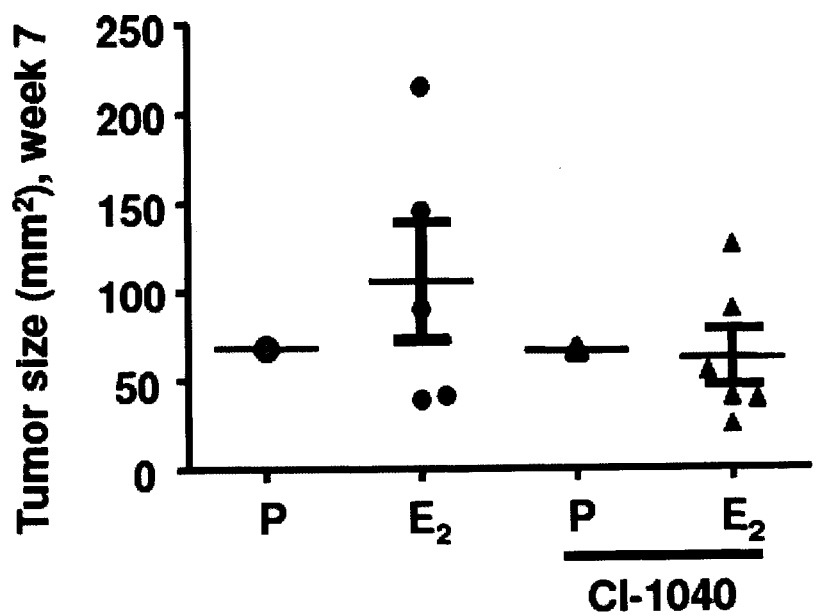
Figure 6:
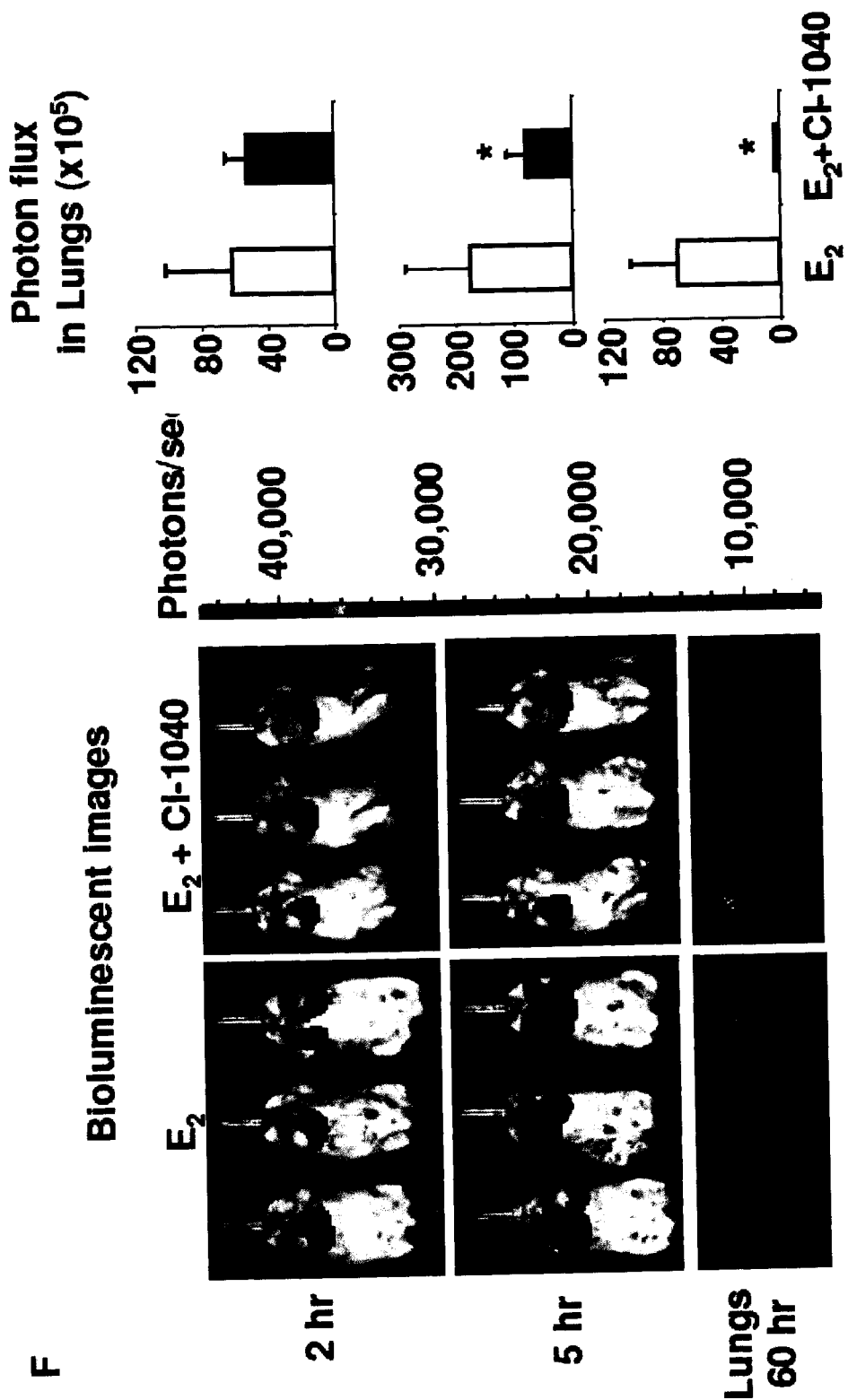

The MEK1/2 Inhibitor CI-1040 Blocks the Estrogen-Driven Metastasis of ELT3 Cells In Vivo These in vitro and in vivo results suggest that $E_2$-induced activation of the MEK/MAPK pathway contributes to the metastatic potential of cir5culating Tsc2-null ELT3 cells. To determine the effect of inhibiting the MEK/MAPK pathway on the pulmonary metastasis of Tsc2-null cells in vivo, we used the inoculation of ELT3 cells, animals, implanted with either placebo or estrogen pellets, were treated with CI-1040 (150 mg/kg day by gavage, twice a day) (Sebolt-Leopold, J. S. et al., 5: 810-816 (1999)). CI-1040 delayed tumor formation (FIG. 6A) and reduced the size of primary tumors by 25% in $E_2$ animals (FIG. 6B), although these data did not reach statistical significance. CI-1040, however, significantly reduced the levels of circulating ELT3 cells in the blood of $E_2$-treated animals by 84% (P=0.042, FIG. 6C). Most strikingly, no lung metastases were detected in mice treated with $E_2$ plus CI-1040 (P=0.046, FIGS. 6D and E).

To investigate further the role of MEK/ERK on the survival of ELT3 cells in the circulation, ELT3-luciferase cells were intravenously injected into mice treated with $E_2$ along or $E_2$ plus CI-1040. At 2 h post-cell injection, similar levels of bioluminescence were observed in the chest regions of all mice. At 5 h, the bioluminescence in the chest regions of the $E_2$ plus CI-1040 treated mice was decreased by 55%, as compared to that in the $E_2$-treated mice (P=0.02, FIG. 6F). After sacrifice at 60 h postcell injection, the bioluminescent signals in the ex vivo lungs of the $E_2$ plus CI-1040-treated mice were significantly reduced by 96%, as compared to the signals in the $E_2$-treated animals (P=0.0045, FIG. 6F).

It will be appreciated from the foregoing results that estrogen treatment of both female and male mice bearing Tsc2-null ELT3 xenograft tumors results in an increase in pulmonary metastases. The estrogen-driven metastasis of ELT3 cells was associated with activation of p42/44 MAPK both in vitro and in vivo. Treatment of the mice with the MEK1/2 inhibitor CI-1040 completely blocked the lung metastases in estrogen-treated animals, while causing only a 25% reduction in the size of the primary xenograft tumors, indicating that activation of MEK by $E_2$ is a critical factor in the metastasis of Tsc2-null cells. In contrast to CI-1040, the mTOR inhibitor RAD001 completely blocked formation of the primary tumor.

Estrogen is known to activate the MAPK pathway (Magliaccio, A. et al., EMBO J., 15: 1292-1300 (1996); Razandi, M. et al., J. Biol. Chem., 278: 2701-2712 (2003); Song, R. X. et al., Mol. Endocrinol., 16: 116-127 (2002); Song, R. X. et al., Endocrinology, 148: 4091-4101 (2007)). It is hypothesized that tuberin-null cells may be particularly sensitive to activation of the Raf/MEK/MAPK signaling cascade by estrogen, because at baseline this signaling pathway is inhibited by Rheb, the target of tuberin's GTPase activating protein domain (Im, E. et al., supra; Karbowniczek, M. et al., supra (2004); Karbowniczek, M., supra (2006)). Metastasis is a complex process, and there are numerous mechanisms through which estrogen's activation of MEK may enhance the metastasis of Tsc2-null cells. The in vitro studies described herein revealed that estrogen induces resistance to anoikis in Tsc2-null cells, which suggests that one of these mechanisms involves the survival of detached cells. This is consistent with our finding of markedly elevated levels of circulating tumor cells in estrogen-treated mice bearing xenograft tumors. We also found that estrogen treatment enhances the survival of intravenously injected cells in the peripheral blood. These data are of particular interest because circulating LAM cells can be detected in the blood and pleural fluid of women with LAM (Crooks, D. M. et al., supra). Our data provide a rationale for the potential use of circulating cells as a quantitative and rapid biomarker of response to targeted therapy in women with LAM.

In addition to promoting the levels of ELT3 cells in the peripheral blood, as measured by real-time RT-PCR using rat-specific primers, estrogen also enhanced the survival of intravenously injected luciferase-expressing ELT3 cells within the lungs. Three hours after injection, there was significantly more bioluminescence in the chest regions of the $E_2$-treated animals, and by 24 h this differences was even more marked. Importantly, however, 1 h after the i.v. injection of ELT3-luciferase cells, similar levels of bioluminescence were present in the lungs of estrogen=-treated and placebo-treated animals, which demonstrates that similar numbers of injected cells reach the lungs. These data suggest that $E_2$ promotes the survival of Tsc2-null cells within the lungs.

The lack of an in vivo model of LAM has been a significant barrier in LAM research. While not a perfect surrogate, ELT3 cells have important features in common with LAM cells, including loss of Tsc2, activation of mTOR, and expression of estrogen receptor alpha and smooth muscle markers (Howe, S. R. et al., Am. J. Pathol., supra (1995); Howe, S. R., Endocrinology, supra (1995)).

The animal model described herein provides a useful tool for screening candidate inhibitors that target signaling pathways and hormonally-driven events.

A number of patent and non-patent publications are cited throughout the foregoing specification in order to describe the state of the art to which this invention pertains. The entire disclosure of each of these publications is incorporated by reference herein.

While certain embodiments of the present invention have been described and/or exemplified above, various other embodiments will be apparent to those skilled in the art from the foregoing specification. For example, the compounds of Formula I, above, may be effective for the treatment of other estrogen-mediated malignancies, such as breast or ovarian cancer. The present invention is, therefore, not limited to the particular embodiments described and/or exemplified, but is capable of considerable variation and modification without departure from the scope of the appended claims.

What is claimed is:

1. A method for the treatment of lymphangioleiomyomatosis (LAM) comprising administering to a patient in need of said treatment a therapeutically effective amount of a compound having the formula:

wherein:

$R_1$ is hydrogen, hydroxy, $C_1$-$C_8$ alkyl, $C_1$-$C_8$ alkoxy, halo, trifluoromethyl, or CN;

$R_2$ is hydrogen;

$R_3$, $R_4$, and $R_5$ independently are hydrogen, hydroxy, halo, trifluoromethyl, $C_1$-$C_8$ alkyl, $C_1$-$C_8$ alkoxy, nitro, CN, or (O or NH)$_m$—(CH$_2$)$_n$—$R_9$, where $R_9$ is hydrogen, hydroxy, $CO_2H$ or $NR_{10}R_{11}$;

n is 0 to 4;

m is 0 or 1;

$R_{10}$ or $R_{11}$ independently are hydrogen or $C_1$-$C_8$ alkyl, or taken together with the nitrogen to which they are attached can complete a 3- to 10-member cyclic ring optionally containing one, two, or three additional heteroatoms selected from O, S, NH, or N—$C_1$-$C_8$ alkyl;

$R_6$ is hydrogen, $C_1$-$C_8$ alkyl, $$\overset{O}{\underset{}{\|}}C-C_1-C_8 \text{ alkyl,}$$

aryl, aralkyl, or $C_3$-$C_{10}$ cycloalkyl;

$R_7$ is hydrogen, $C_1$-$C_8$ alkyl, $C_2$-$C_8$ alkenyl, $C_2$-$C_8$ alkynyl, $C_3$-$C_{10}$ cycloalkyl (or cycloalkyl optionally containing a heteroatom selected from O, S, or $NR_9$);

X is bromine or iodine;

and wherein any of the foregoing alkyl, alkenyl, and alkynyl groups can be unsubstituted or substituted by cycloalkyl (or cycloalkyl optionally containing a heteroatom selected from O, S, or $NR_9$), aryl, aryloxy, heteroaryl, or heteroaryloxy; or $R_6$ and $R_7$ taken together with the N—O to which they are attached can complete a 5- to 10-membered cyclic ring, optionally containing one, two, or three additional heteroatoms selected from O, S, or $NR_{10}R_{11}$.

2. The method of claim 1, wherein said compound is formulated with a pharmaceutically acceptable carrier medium for administration to said patient.

3. The method of claim 1, wherein said compound is 2-(2-Chloro-4-iodo-phenylamino)-N-cyclopropylmethoxy-3,4-difluoro-benzamide.

4. The method of claim 1, wherein said patient is a mammal.

5. The method of claim 1, wherein said patient is a human.

6. The method of claim 1 further comprising administration of at least one mTOR inhibitor.

7. The method of claim 6, wherein said mTOR inhibitor is RAD001.

8. The method of claim 2, wherein said compound is 2-(2-Chloro-4-iodo-phenylamino)-N-cyclopropylmethoxy-3,4-difluoro-benzamide.

* * * * *

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: mouse forward primer

<400> SEQUENCE: 1
ggcatcttct gctggctcc                                               19

<210> SEQ ID NO 2
<211> LENGTH: 21
<212> TYPE: DNA
<213> ORGANISM: Artificial Sequence
<220> FEATURE:
<223> OTHER INFORMATION: mouse reverse primer

<400> SEQUENCE: 2
ggctagaacc ctccccattc t                                            21

<210> SEQ ID NO 3
<211> LENGTH: 26
<212> TYPE: DNA
<213> ORGANISM: Artificial Sequence
<220> FEATURE:
<223> OTHER INFORMATION: mouse probe

<400> SEQUENCE: 3
cactccatcg cttatcgctg caagtg                                       26

<210> SEQ ID NO 4
<211> LENGTH: 22
<212> TYPE: DNA
<213> ORGANISM: Artificial Sequence
<220> FEATURE:
<223> OTHER INFORMATION: rat forward primer
```

```
<400> SEQUENCE: 4
caagacggat gatcaaaatg tg                                          22

<210> SEQ ID NO 5
<211> LENGTH: 25
<212> TYPE: DNA
<213> ORGANISM: Artificial Sequence
<220> FEATURE:
<223> OTHER INFORMATION: rat reverse primer

<400> SEQUENCE: 5
tctctgtttt aatctttgcc tctcc                                       25

<210> SEQ ID NO 6
<211> LENGTH: 32
<212> TYPE: DNA
<213> ORGANISM: Artificial Sequence
<220> FEATURE:
<223> OTHER INFORMATION: rat probe

<400> SEQUENCE: 6
cctgccaagg gtattctttt tcctcattta aa                               32
```